US011285183B2

(12) United States Patent
Ko et al.

(10) Patent No.: US 11,285,183 B2
(45) Date of Patent: Mar. 29, 2022

(54) LACTOBACILLUS GASSERI KBL697 STRAIN AND USE THEREOF

(71) Applicant: KoBioLabs, Inc., Seoul (KR)

(72) Inventors: Woo Ri Ko, Seoul (KR); June Chul Lee, Gyeonggi-do (KR); Hyo In Park, Seoul (KR); Tae Wook Nam, Gyeonggi-do (KR); Gwang Pyo Ko, Seoul (KR); Woon Ki Kim, Seoul (KR); Dae Hee Han, Seoul (KR); In Su Kim, Gyeonggi-do (KR); Jin Woo Lee, Gyeonggi-do (KR); Hye Jin Kim, Seoul (KR)

(73) Assignee: KoBioLabs, Inc., Seoul (KR)

( * ) Notice: Subject to any disclaimer, the term of this patent is extended or adjusted under 35 U.S.C. 154(b) by 0 days.

(21) Appl. No.: 17/102,301

(22) Filed: Nov. 23, 2020

(65) Prior Publication Data

US 2021/0093682 A1     Apr. 1, 2021

Related U.S. Application Data

(63) Continuation of application No. PCT/KR2019/006232, filed on May 23, 2019.

(30) Foreign Application Priority Data

May 23, 2018 (KR) .................... 10-2018-0058568

(51) Int. Cl.
*A61K 35/747*    (2015.01)
*A23L 33/135*    (2016.01)
*A61K 8/02*      (2006.01)

(52) U.S. Cl.
CPC .......... *A61K 35/747* (2013.01); *A23L 33/135* (2016.08); *A61K 8/0208* (2013.01)

(58) Field of Classification Search
None
See application file for complete search history.

(56) References Cited

U.S. PATENT DOCUMENTS

| 7,195,906 | B2 | 3/2007 | Collins et al. |
| 8,021,868 | B2 | 9/2011 | Su et al. |
| 8,936,783 | B2 | 1/2015 | Alenfall et al. |
| 9,314,041 | B2 | 4/2016 | Sashihara et al. |
| 10,052,354 | B2 | 8/2018 | Tobita et al. |
| 2008/0107699 | A1* | 5/2008 | Spigelman ........... A61K 35/747 424/404 |
| 2012/0190634 | A1 | 7/2012 | Chung et al. |
| 2012/0258126 | A1 | 10/2012 | Schøller et al. |
| 2014/0072544 | A1 | 3/2014 | Dimitrov et al. |

FOREIGN PATENT DOCUMENTS

| EP | 0415941 | 6/1993 |
| EP | 0554418 | 3/1998 |
| EP | 1778258 B1 | 1/2009 |
| JP | 2008099632 A1 | 5/2008 |
| JP | 2008169198 A | 7/2008 |
| JP | 2010130954 A | 6/2010 |
| JP | 2011200211 A | 10/2011 |
| KR | 1020080080981 A | 9/2008 |
| KR | 1020110021699 A | 3/2011 |
| KR | 1020120125359 | 11/2012 |
| KR | 1020130115943 | 10/2013 |
| KR | 1020140040731 | 4/2014 |
| KR | 1020170049216 | 5/2017 |
| KR | 1020170054460 | 5/2017 |
| KR | 102063554 B1 | 1/2020 |
| WO | 96029083 | 9/1996 |
| WO | 2006013441 A2 | 2/2006 |

OTHER PUBLICATIONS

International Preliminary Report on Patentability for International Application No. PCT/KR2019/006232 "Lactobacillus Gasseri KBL697 Strain and Use Thereof" dated Nov. 24, 2020.
Written Opinion for International Application No. PCT/KR2019/006232 "Lactobacillus Gasseri KBL697 Strain and Use Thereof" dated Aug. 28, 2019.
Kim K et al., "Inhibitory mechanism of anti-allergic peptides in RBL2H3 cells", Eur J Pharmacol, 581:191-203, 2008.
International Search Report for International Application No. PCT/KR2019/006232 "Lactobacillus Gasseri KBL697 Strain and Use Thereof" Aug. 28, 2019.
NCBI. GenBank Accession No. CP021427.I. Lactobacillus gasseri strain 4MI3, complete genome, May 30, 2017.
Song, H., et al., "*Faecalibacterium prausnitzii* subspecies-level dysbiosis in the human gut microbiome underlying atopic dermatitis", J. Allergy Clin Immunol, Mar. 2016, 137(3): 852-860.
Search Report for Russian Application No. 2020139906, "Lactobacillus Gasseri KBL697 Strain and Use Thereof" date of completion: Oct. 15, 2021.
NCBI, Genbank Accession No. KY969250.1 "Lactobacillus gasseri strain JN 16S ribosomal RNA gene, partial sequence" Apr. 20, 2017.
News Article Lactobacillus, "kills dandruff" (Mar. 30, 2018).

* cited by examiner (Continued)

*Primary Examiner* — Mary Maille Lyons
(74) *Attorney, Agent, or Firm* — Hamilton, Brook, Smith & Reynolds, P.C.

(57) ABSTRACT

A strain of *Lactobacillus gasseri* KBL697 and the use thereof are described. The strain of *Lactobacillus gasseri* KBL697 (Accession No. KCTC 13520BP) attenuates allergic reactions of cells, significantly improves symptoms of atopic dermatitis, and exhibits anti-inflammatory and anti-fungal effects and a therapeutic effect for intestinal diseases such as irritable bowel syndrome and colitis. Thus, the single strain alone can achieve all the purposes of alleviating allergic diseases and inflammatory diseases and improving intestinal health, thereby finding advantageous applications as a probiotic substance. In addition, the strain, based on the anti-fungal activity thereof, can be advantageously utilized in a skin external preparation against various skin diseases caused by fungi, and in a cosmetic composition and a functional patch for alleviating sensitive skin.

17 Claims, 12 Drawing Sheets

Specification includes a Sequence Listing.

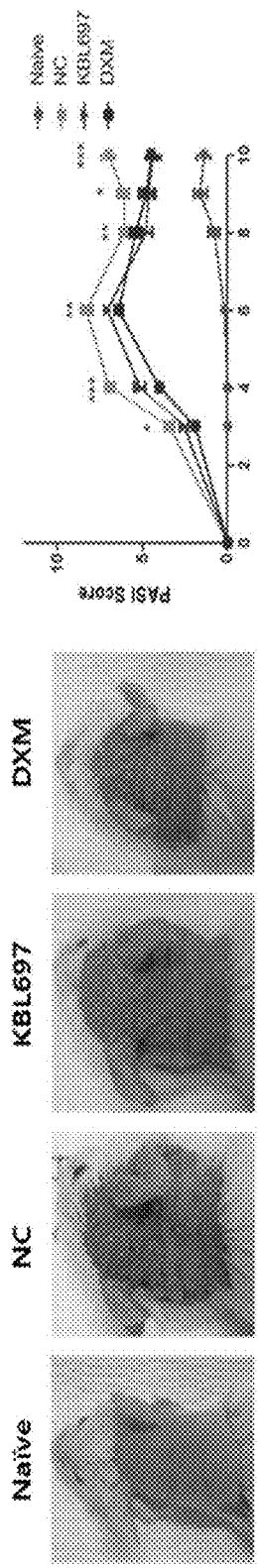
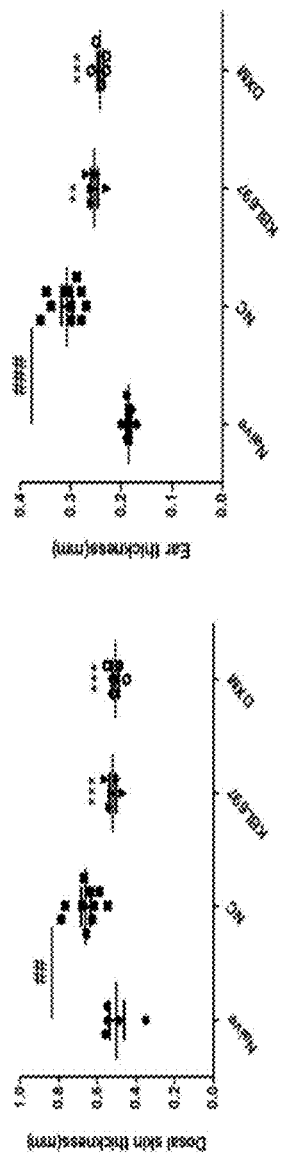
FIG. 16A  FIG. 16B  FIG. 16C  FIG. 16D  FIG. 16E
FIG. 16F
FIG. 16G

```
SEQUENCE LISTING

<160> NUMBER OF SEQ ID NOS: 1

<210> SEQ ID NO 1
<211> LENGTH: 1482
<212> TYPE: DNA
<213> ORGANISM: Lactobacillus gasseri

<400> SEQUENCE: 1
ggcaagtggg cggcgtgcta tacatgcagt cgagcgagct tgcctagatg aatttggtgc      60
ttgcaccaaa tgaaactaga tacaagcgag cggcggacgg gtgagtaaca cgtgggtaac     120
ctgcccaaga gactgggata acacctggaa acagatgcta ataccggata acaacactag     180
acgcatgtct agagtttaaa agatggttct gctatcactc ttggatggac ctgcggtgca     240
ttagctagtt ggtaaggcaa cggcttacca aggcaatgat gcatagccga gttgagagac     300
tgatcggcca cattgggact gagacacggc ccaaactcct acgggaggca gcagtaggga     360
atcttccaca atggacgcaa gtctgatgga gcaacgccgc gtgagtgaag aagggtttcg     420
gctcgtaaag ctctgttggt agtgaagaaa gatagaggta gtaactggcc tttatttgac     480
ggtaattact tagaaagtca cggctaacta cgtgccagca gccgcggtaa tacgtaggtg     540
gcaagcgttg tccggattta ttgggcgtaa agcgagtgca ggcggttcaa taagtctgat     600
gtgaaagcct tcggctcaac cggagaattg catcagaaac tgttgaactt gagtgcagaa     660
gaggagagtg gaactccatg tgtagcggtg gaatgcgtag atatatggaa gaacaccagt     720
ggcgaaggcg gctctctggt ctgcaactga cgctgaggct cgaaagcatg ggtagcgaac     780
aggattagat accctggtag tccatgccgt aaacgatgag tgctaagtgt tgggaggttt     840
```

```
ccgcctctca gtgctgcagc taacgcatta agcactccgc ctggggagta cgaccgcaag    900
gttgaaactc aaaggaattg acgggggccc gcacaagcgg tggagcatgt ggtttaattc    960
gaagcaacgc gaagaacctt accaggtctt gacatccagt gcaaacctaa gagattagga   1020
gttcccttcg gggacgctga gacaggtggt gcatggctgt cgtcagctcg tgtcgtgaga   1080
tgttgggtta agtcccgcaa cgagcgcaac ccttgtcatt agttgccatc attaagttgg   1140
gcactctaat gagactgccg gtgacaaacc ggagaaaggt ggggatgacg tcaagtcatc   1200
atgcccctta tgacctgggc tacacacgtg ctacaatgga cggtacaacg agaagcgaac   1260
ctgcgaaggc aagcggatct ctgaaagccg ttctcagttc ggactgtagg ctgcaactcg   1320
cctacacgaa gctggaatcg ctagtaatcg cggatcagca cgccgcggtg aatacgttcc   1380
cgggccttgt acacaccgcc cgtcacacca tgagagtctg taacacccaa agccggtggg   1440
ataaccttta taggagtcag ccgtctaagt agacagatgt ta                     1482
```

LACTOBACILLUS GASSERI KBL697 STRAIN AND USE THEREOF

RELATED APPLICATIONS

This application is a continuation of International Application No. PCT/KR2019/006232, which designates the United States and was filed on May 23, 2019, published in Korean and claims priority under 35 U.S.C. § 119 or 365 to Korean Application No. 10-2018-0058568, filed May 23, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 58881002001_SEQUENCELISTING; created Nov. 19, 2020, 3 KB in size.

TECHNICAL FIELD

The present invention relates to a strain of *Lactobacillus gasseri* KBL697 and the use thereof. More specifically, the present invention relates to a health functional food composition having at least one effect selected from the group consisting of alleviation of allergic symptoms, alleviation of inflammatory symptoms, improvement of intestinal health, and immunoregulation; an anti-fungal composition; and a pharmaceutical composition for the treatment of at least one disease selected from the group consisting of allergic diseases, inflammatory diseases, intestinal diseases, and autoimmune diseases, comprising at least one selected from the group consisting of a novel probiotic strain of *Lactobacillus gasseri* KBL697, cultures of said strain, lysates of said strain, and extracts of said strain.

BACKGROUND ART

Probiotics refer to microorganisms and the resulting products therefrom having antimicrobial activities and enzyme activities to help the balance of intestinal microorganisms. In addition, probiotics are also defined as live bacteria in the form of a single or multiple strain(s) to improve intestinal flora when provided to human or animals in the form of dry cells or fermentation products. Probiotics must inhabit the human gut, be non-pathogenic and non-toxic, and survive long enough until they arrive at the intestine. Further, probiotics must maintain viability and activities until they are consumed in the food delivered, be sensitive to antibiotics used to prevent infection, and do not have antibiotic-resistant plasmids. Also, probiotics must be resistant to acids, enzymes, and bile in the intestinal environment.

These probiotics may include, for example, *Bacillus* sp. having an excellent ability to produce digestive enzymes such as amylase, protease, lipase, cellulase, and phosphatase, *Lactobacillus* sp. producing lactic acid, and photosynthetic bacteria preventing stink by way of using the stink-causing substances (such as ammonia, hydrogen sulfide, and amines) remaining in the feces of livestock in metabolic process. Recently, probiotics have been reported to have various health function improvement effects including improvement of intestinal health, and thereby spotlighted as major therapeutic substances which can replace existing compound-based therapeutic agents.

Meanwhile, allergy is a biochemical phenomenon that exhibits a unique, altered response to a foreign substance (antigen, allergen). The foreign substance which causes symptoms is called allergen, while the diseases from those symptoms are called allergic diseases. Allergy is a pathological process in the living body resulting from the antigen-antibody reaction. In general, there are four types of allergies depending on the period to trigger the reaction and the complement involvement. Type 1, among those, is anaphylactic type (immediate type) in which target organs are mostly digestive organs, skin and lungs, and the common symptoms include gastrointestinal allergy, urticaria, atrophodermatitis, allergic rhinitis, and bronchial asthma, etc. The pathological mechanism of Type 1 is known as follows: when antigens contact IgE antibodies attached to the surface of mast cells and basophilic leukocytes, the target cells are activated to secrete chemical transmitters such as histamine, leukotriene, and PAF, and then blood vessels and smooth muscles are contracted. Such mechanism can be often combined with Type 4 (delayed type). In other words, such anaphylaxis and allergic reaction can arise due to a variety of changes in the mast cells, etc. The activation of mast cells, which leads to degranulation, is caused by binding of antigen, anti-IgE, lectin, etc. to Fc receptors, stimulation of anaphylatoxin, etc., or other drugs such as calcium ionophore, compound 48/80, codeine and synthetic adrenocorticotropic hormone.

Mast cells and basophil leukocytes in blood are known as main cells in the body to cause many allergic diseases such as allergic rhinitis, allergic dermatitis, asthma, food allergy and anaphylactic shock. These cells have receptors (FcRI) on their surfaces for IgE which is an antibody causing allergy, and the cells are stimulated by the allergy-causing substances (antigen, allergen) to secrete their own various allergy-causing substances out of the cells (Kim K et al, Eur J Pharmacol, 581:191-203, 2008).

Among allergic diseases, atopic dermatitis, as widely known to the public, is a chronic recurrent skin disease that affects newborns or children and may persist until adulthood. Like asthma or allergic rhinitis, atopic dermatitis is an inflammatory skin disease associated with local infiltration of T-lymphocyte which produces IL-4 and IL-5. IL-4, as well known to the public, controls the development of the T helper 2 (Th2) phenotype, resulting in overproduction of immunoglobulins (Ig) and eosinophilia, and increase of serum IgE levels. 80-90% of the subjects who were positive to the skin test regarding food and inhalant allergens were found to have atopic dermatitis.

There are different treatments for treating or preventing allergic diseases and atopic dermatitis, but no effective treatment has been found yet. Some drug-based treatments are known, but even a short term administration of the drug for the treatment would develop a tolerance and a long-term administration may cause serious side effects, and thus such drug-based treatments of allergic diseases and atopic dermatitis have been avoided recently. Under the circumstances, without treatment having any absolute, obvious effect, irritating symptoms such as itching and redness of skin in addition to allergy often fail to improve.

Meanwhile, irritable bowel syndrome (IBS) is a symptom characterized by abdominal pain, and/or irritations associated with changed intestinal movement or bowel habits, such symptoms cannot be explained with anatomic or biochemical abnormality. Common symptoms of IBS also include urinary urgency, bloating and feeling of incomplete intestinal movement. Accordingly, IBS can be classified as functional gastrointestinal disorders comprising conditions such as functional bloating, non-cardiac chest pain, non-ulcerative dyspepsia, and chronic constipation or diarrhea. In particular, in the case of IBS, since the related symptoms affect both well-being and normal function aspects of patients, the disease has a huge impact on morbidity and quality of life, beyond abdominal pain and discomfort.

Inflammatory bowel disease (IBD) is a condition in which abnormal chronic inflammation in the intestine repeats improvement and recurrence, comprising all intestinal inflammatory diseases, such as Crohn's disease, ulcerative colitis, or Behcet's disease, but not limited thereto. Many researches have been conducted in the field of drug development to treat IBS and IBD. In this regard, various antidepressants are commonly used, even though the efficacy thereof in clinical trials is moderate and the clinical utility thereof is limited due to significant side effects. Serotonergic medications have also been proved to have efficacy against overall IBS symptoms. However, the application of these medications has been restricted in various ways due to recent several safety problems. Accordingly, there is increasing interest in developing a new therapeutic agent for IBS.

WO 96/29083 and EP 554418 disclose two types of Lactobacillus strains which form colonies in bowel, i.e., Lactobacillus plantarum 299v (DSM 6595) and Lactobacillus casei ssp. rhamnosus 271 (DSM 6594), etc. EP 415941 discloses a method for preparing a nutrient composition, comprising treating oat gruel with enzymes before mixing it with lactobacilli. U.S. Pat. No. 7,195,906 discloses a strain of Bifidobacterium isolated from resected and washed human gastrointestinal tract for the treatment of inflammatory diseases, especially gastrointestinal inflammatory activity such as IBD and IBS.

However, no strain having excellent effects on improving intestinal health, for example, treatment of IBD and IBS has been found yet, and in order to find strains having such effects, many research institutions have been working on.

Under the circumstances, the present inventors devoted themselves to studies of probiotics to find a way to replace drug-based treatments for allergic diseases, including atopic dermatitis, which have no satisfactory treatments. And therefore, the present invention was completed by confirming that a novel strain of Lactobacillus gasseri showed excellent therapeutic effects on allergic diseases such as atopic dermatitis, and further confirming that said strain also showed superior effects on anti-fungal activity, intestinal health, immunoregulation, and inhibition of inflammation.

SUMMARY

The purpose of the present invention is to provide a novel strain showing excellent effects on alleviation of allergic symptoms such as atopic dermatitis, alleviation of inflammatory symptoms, anti-fungal activity, improvement of intestinal health, and immunoregulation, and a variety of uses thereof.

In order to achieve the purpose, the present invention provides Lactobacillus gasseri KBL697 strain (Accession No. KCTC 13520BP).

Also, the present invention provides a food composition or food additive composition comprising at least one selected from the group consisting of said strain, cultures of said strain, lysates of said strain, and extracts of said strain.

The present invention provides a feed composition or feed additive composition comprising at least one selected from the group consisting of said strain, cultures of said strain, lysates of said strain, and extracts of said strain.

The present invention also provides an anti-fungal composition, such as an anti-dandruff composition, comprising at least one selected from the group consisting of said strain, cultures of said strain, lysates of said strain, and extracts of said strain.

The present invention also provides a pharmaceutical composition for the treatment of allergic diseases such as atopic dermatitis, inflammatory diseases, intestinal diseases and/or autoimmune diseases, comprising at least one selected from the group consisting of said strain, cultures of said strain, lysates of said strain, and extracts of said strain.

The present invention also provides a method for treating allergic diseases including atopic dermatitis, inflammatory diseases, intestinal diseases and/or autoimmune diseases, comprising administering at least one selected from the group consisting of said strain, cultures of said strain, lysates of said strain, and extracts of said strain to a subject in need thereof.

The present invention also provides a composition comprising at least one selected from the group consisting of said strain, cultures of said strain, lysates of said strain, and extracts of said strain, for the use of preventing or treating allergic diseases including atopic dermatitis, inflammatory diseases, intestinal diseases and/or autoimmune diseases.

The present invention also provides the use of a composition for preparing a preventive or therapeutic drug for allergic diseases including atopic dermatitis, inflammatory diseases, intestinal diseases and/or autoimmune diseases, comprising at least one selected from the group consisting of said strain, cultures of said strain, lysates of said strain, and extracts of said strain.

The present invention also provides a cosmetic composition comprising at least one selected from the group consisting of said strain, cultures of said strain, lysates of said strain, and extracts of said strain.

The present invention also provides a cosmetic patch or a medical patch comprising at least one selected from the group consisting of said strain, cultures of said strain, lysates of said strain, and extracts of said strain.

BRIEF DESCRIPTION OF DRAWINGS

FIGS. 16A-16G illustrate the results of observation of the alleviating effect of PASI (Psoriasis Area and Severity Index) and edema symptoms by *Lactobacillus gasseri* KBL697 strain in mouse models that psoriasis was induced.

BEST MODE

Figure 1:
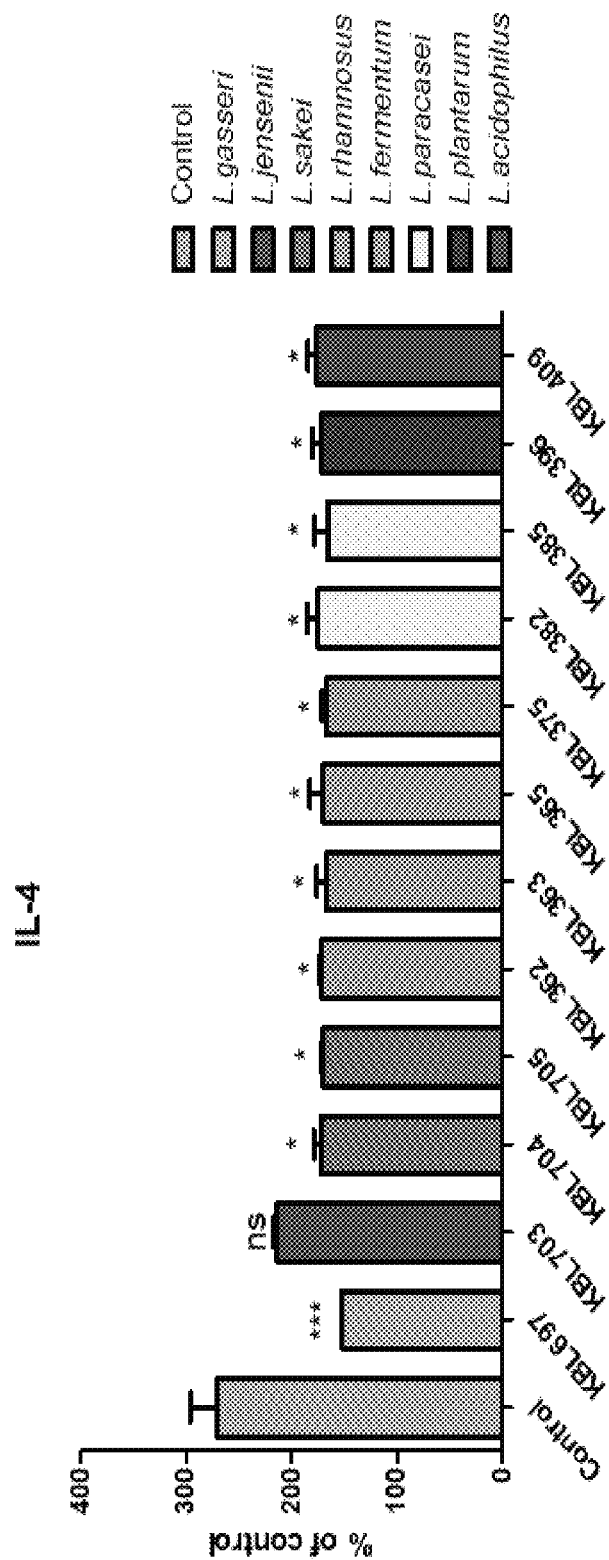
FIG. 1 illustrates the result confirming the inhibitory effect of IL-4 expression by various Lactobacillus strains including Lactobacillus gasseri KBL697 strain, after inducing allergic reaction in EL4 cell lines.

Unless defined otherwise, all of the technical, scientific terms used in the present specification mean the same as understood by a person having ordinary skills in the art ("those skilled in the art"). In general, the nomenclature used in the present specification is well known in the art and commonly used.

The present invention has found an anti-allergic effect of microorganisms derived from the human body, and selected *Lactobacillus gasseri* KBL697 strain (Accession No. KCTC 13520BP) having excellent allergy inhibitory effects. Analysis of 16S rDNA of said strain demonstrates that said strain is a novel strain which has never been known to the public. According to one embodiment of the present invention, the present invention relates to a novel probiotic strain of *Lactobacillus gasseri* KBL697 (Accession No. KCTC 13520BP), and said strain is characterized by comprising 16S rDNA sequence of SEQ ID NO: 1.

```
16S rDNA sequence of a strain of Lactobacillus
gasseri KBL697 (Accession No. KCTC 13520BP)
                                      <SEQ ID NO: 1>
GGCAAGTGGGCGGCGTGCTATACATGCAGTCGAGCGAGCTTGCCTAGATG

AATTTGGTGCTTGCACCAAATGAAACTAGATACAAGCGAGCGGCGGACGG

GTGAGTAACACGTGGGTAACCTGCCCAAGAGACTGGGATAACACCTGGAA

ACAGATGCTAATACCGGATAACAACACTAGACGCATGTCTAGAGTTTAAA

AGATGGTTCTGCTATCACTCTTGGATGGACCTGCGGTGCATTAGCTAGTT

GGTAAGGCAACGGCTTACCAAGGCAATGATGCATAGCCGAGTTGAGAGAC

TGATCGGCCACATTGGGACTGAGACACGGCCCAAACTCCTACGGGAGGCA

GCAGTAGGGAATCTTCCACAATGGACGCAAGTCTGATGGAGCAACGCCGC

GTGAGTGAAGAAGGGTTTCGGCTCGTAAAGCTCTGTTGGTAGTGAAGAAA

GATAGAGGTAGTAACTGGCCTTTATTTGACGGTAATTACTTAGAAAGTCA

CGGCTAACTACGTGCCAGCAGCCGCGGTAATACGTAGGTGGCAAGCGTTG

TCCGGATTTATTGGGCGTAAAGCGAGTGCAGGCGGTTCAATAAGTCTGAT

GTGAAAGCCTTCGGCTCAACCGGAGAATTGCATCAGAAACTGTTGAACTT

GAGTGCAGAAGAGGAGAGTGGAACTCCATGTGTAGCGGTGGAATGCGTAG

ATATATGGAAGAACACCAGTGGCGAAGGCGGCTCTCTGGTCTGCAACTGA

CGCTGAGGCTCGAAAGCATGGGTAGCGAACAGGATTAGATACCCTGGTAG

TCCATGCCGTAAACGATGAGTGCTAAGTGTTGGGAGGTTTCCGCCTCTCA

GTGCTGCAGCTAACGCATTAAGCACTCCGCCTGGGGAGTACGACCGCAAG

GTTGAAACTCAAAGGAATTGACGGGGGCCCGCACAAGCGGTGGAGCATGT

GGTTTAATTCGAAGCAACGCGAAGAACCTTACCAGGTCTTGACATCCAGT

GCAAACCTAAGAGATTAGGAGTTCCCTTCGGGGACGCTGAGACAGGTGGT

GCATGGCTGTCGTCAGCTCGTGTCGTGAGATGTTGGGTTAAGTCCCGCAA

CGAGCGCAACCCTTGTCATTAGTTGCCATCATTAAGTTGGGCACTCTAAT

GAGACTGCCGGTGACAAACCGGAGAAAGGTGGGGATGACGTCAAGTCATC

ATGCCCCTTATGACCTGGGCTACACACGTGCTACAATGGACGGTACAACG

AGAAGCGAACCTGCGAAGGCAAGCGGATCTCTGAAAGCCGTTCTCAGTTC

GGACTGTAGGCTGCAACTCGCCTACACGAAGCTGGAATCGCTAGTAATCG

CGGATCAGCACGCCGCGGTGAATACGTTCCCGGGCCTTGTACACACCGCC

CGTCACACCATGAGAGTCTGTAACACCCAAAGCCGGTGGGATAACCTTTA

TAGGAGTCAGCCGTCTAAGTAGACAGATGTTA
```

Then, the present invention conducted experiments regarding the efficacy of said strain, and thereby verified that said strain has an excellent inhibitory effect on allergies such as atopic dermatitis, alleviates the inflammatory reaction, and has an anti-fungal activity, immunoregulatory properties and therapeutic effects on intestinal diseases. Further, the inventors confirmed that said effects could be provided not only in the condition of living bacteria but also under the low temperature sterilization or the high temperature sterilization.

Accordingly, in another embodiment of the present invention, the present invention relates to a food composition or food additive composition comprising at least one selected from the group consisting of *Lactobacillus gasseri* KBL697 strain (Accession No. KCTC 13520BP), cellular components of said strain, cultures of said strain, lysates of said strain, and extracts of said strain.

The composition can be characterized in that it is a health functional food composition having at least one effect selected from the group consisting of alleviation of allergic symptoms such as atopic dermatitis, alleviation of inflammatory symptoms, improvement of intestinal health, and immunoregulation.

Said food composition or food additive composition can be readily utilized as the food effective for alleviation of allergic symptoms such as atopic dermatitis, alleviation of inflammatory symptoms, improvement of intestinal health and/or immunoregulation, and for the prevention thereof, for example, as main ingredients or minor ingredients of food, food additives, health functional food composition or functional beverages, but not limited thereto.

The term "food composition" refers to a natural or artificial product comprising at least one nutrient, and more preferably, refers to a product which became edible through certain processing, usually encompassing all of food, food additives, health functional food and functional beverages.

The food that may comprise the said food composition according to the present invention as an additive may include, for example, different types of food, beverages, chewing gum, tea, vitamin complex, or functional food. In addition, the food of the present invention includes special nutritional food (e.g., modified milk, infant/baby food), processed meat products, fish meat products, tofu, muk, noodles (e.g., ramen, Asian noodles), bakery products, health supplement food, seasoning products (e.g., soy sauce, soybean paste, red pepper paste, mixed paste), sauces, confectionery (e.g., snack foods), candies, chocolates, chewing gums, ice-creams, milk products (e.g., fermented milk, cheese), other processed food, Kim-chi, salted food (e.g., different types of Kim-chi, pickled food), beverages (e.g., fruit juice, vegetable juice, soy milk, fermented beverages), and natural seasonings (e.g., broth powder for ramen), but not limited thereto. Said food, beverages or food additives can be prepared in conventional manners.

The term "health functional food" is a group of food to which value is added so as for the function thereof to be exerted and expressed for the predetermined purpose by using physical, biochemical or bioengineering techniques thereto, or a processed food designed so as for the in-vivo adjustment functions of the relevant food composition such as rhythm adjustment in prophylaxis, prevention of disease and recovery from disease to be sufficiently expressed. Such functional food may comprise food supplement additives which are food-scientifically acceptable, and may additionally comprise suitable carriers, excipients and diluents, which are commonly used in the manufacturing thereof.

The term "functional beverages", as used in the present invention, collectively refer to the drink products to relieve thirst or to enjoy the taste. There is no particular limitation thereto, except that, as essential ingredients of the indicated ratio, a composition for alleviation of allergic symptoms such as atopic dermatitis, alleviation of inflammatory symptoms, improvement of intestinal health and/or immunoregulation and the prevention thereof should be comprised in the beverages, and various flavoring agents or natural carbohydrates may be contained therein as additional ingredients like in common beverages.

In addition to the above, the food comprising the food composition or the food additive composition according to the present invention may contain various nutrients, vitamins, minerals (electrolyte), flavoring agents such as synthetic flavoring agents and natural flavoring agents, coloring agents and fillers (cheese, chocolate, etc.), pectic acid and salts thereof, alginic acid and salts thereof, organic acids, protective colloidal thickening agents, pH controlling agents, stabilizing agents, preservatives, glycerin, alcohol, carbonizing agents as used in carbonated beverages and the like, and each of the above ingredients may be used alone or in combination with each other.

In the food comprising the food composition according to the present invention, the composition of the present invention may be comprised in an amount of 0.001% by weight to 100% by weight, and preferably 1% by weight to 99% by weight, based on the total weight of the food; in the case of beverages, it may be comprised at an amount of 0.001 g to 10 g, and preferably 0.01 g to 1 g, based on 100 ml. For long-term intake for the purpose of health and hygiene or for the purpose of health control, however, the amount may be below the above-mentioned range; and since the effective ingredients have no problem in terms of safety profile, they can be used at an amount above the range and they are not limited to the amount range mentioned above.

The food composition according to the present invention may comprise *Lactobacillus gasseri* KBL697 strain alone or in combination with the acceptable carrier, or may be prepared in the form of the composition suitable for consumption by human or animals. That is, the composition may be added to the food which comprises no probiotic bacteria or a couple of probiotic bacteria. For example, the microorganisms which can be used in combination with the strain according to the present invention in preparing the food of the present invention should be suitable for the consumption by human or animals, and have probiotic activities to inhibit pathogenic, harmful bacteria or to improve the balance of microorganisms in the mammalian intestinal tract, upon intake, but not limited thereto. Such probiotic microorganisms may include, for example, yeast such as *Saccharomyces, Candida, Pichia* or *Torulopsis*, fungi such as *Aspergillus, Rhizopus, Mucor*, or *Penicillium*, and bacteria belonging to the genus of *Lactobacillus, Bifidobacterium, Leuconostoc, Lactococcus, Bacillus, Streptococcus, Propionibacterium, Enterococcus*, or *Pediococcus*. Suitable probiotic microorganisms specifically may include, for example, *Saccharomyces cerevisiae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei, Lactobacillus curvatus, Lactobacillus delbruckii, Lactobacillus johnsonii, Lactobacillus farciminus, Lactobacillus gasseri, Lactobacillus helveticus, Lactobacillus rhamnosus, Lactobacillus reuteri, Lactobacillus sakei, Lactococcus lactis*, or *Pediococcus acidilactici*. Preferably, the food composition according to the present invention may further comprise a probiotic microorganism mixture having excellent probiotic activities and superior activities of anti-allergy, anti-inflammation, immunoregulation and/or improvement of intestinal health to further enhance the effects thereof. The carriers that can be included in the food composition of the present invention may include, for example, extenders, high fiber additives, encapsulating agents, and lipids, which are widely well known in the art. *Lactobacillus gasseri* KBL697 strain in the present invention may be in the lyophilized or encapsulated form or in the form of culture suspensions or dry powders.

The composition of the present invention can also be provided in the form of a feed additive comprising said strain or a feed comprising the same.

The feed additive of the present invention may be in the form of dry or liquid formulation, and further comprise other non-pathogenic microorganisms in addition to the said *Lactobacillus gasseri* KBL697 strain. The microorganisms that can be added to the feed additive may include, for example, *Bacillus subtilis* that can produce protease, lipase and sugar-converting enzymes, *Lactobacillus* strain having a physiological activity and degradability of organic compounds under anaerobic conditions such as in the stomach of cow, filamentous fungi such as *Aspergillus oryzae* showing effects on increasing weight of animals, milk yield, and digestibility of the feed (Slyter, L. L. J. Animal Sci., 1976, 43. 910-926) and yeast such as *Saccharomyces cerevisiae* (Johnson, D. E et al. J. Anim. Sci., 1983, 56, 735-739; Williams, P. E. V. et al, 1990, 211).

The feed additive of the present invention may additionally comprise at least one enzyme agent in addition to said strain of *Lactobacillus gasseri* KBL697. The additional enzyme agents can be in a dry or liquid form, and may include, for example, steatolytic enzymes such as lipase, phytase to produce phosphate and inositol phosphate by degrading phytic acid, amylase, i.e., an enzyme to hydrolyze α-1,4-glycoside bond included in, for example, starch and glycogen, phosphatase, i.e., an enzyme to hydrolyze organic phosphoric acid ester, carboxymethylcellulase to degrade cellulose, xylase to degrade xylose, maltase to hydrolyze maltose into two glucose molecules, and sugar producing enzymes such as invertase to produce glucose-fructose mixture by hydrolyzing saccharose.

In the use of *Lactobacillus gasseri* KBL697 strain of the present invention as feed additives, the raw ingredients for the feed, such as peanuts, peas, beets, pulp, grain by-products, animal guts powder and fish meal powder, including various grains and soybean protein, can be used. They may be processed or not, and can be used without limitation. The processing may include, but not limited thereto, such a process that the raw ingredients of the feed are charged and can be compressed under pressure against a given outlet, and for proteins, extrusion by which proteins are degenerated to increase availability may be preferably used. Extrusion denatures proteins through thermal treatment to destroy antienzyme factors, which is advantageous. Further, for soybean proteins, the digestibility thereof can be improved through extrusion to inactivate anti-nutrients such as a trypsin inhibitor, one of inhibitors of protease that are present in soybeans. Further, extrusion can promote improvement of digestibility by protease, enhancing the nutritional value of soybean proteins.

According to another embodiment of the present invention, the present invention relates to an anti-fungal composition comprising at least one selected from the group consisting of said strain, cultures of said strain, lysates of said strain, and extracts of said strain.

The composition can be characterized by showing an anti-fungal activity on the one selected from the group consisting of *Malassezia furfur*, *Malassezia globosa* and *Malassezia restricta*, but not limited thereto.

The composition can be a composition for preventing, alleviating or treating seborrheic dermatitis or dandruff, and said seborrheic dermatitis can be on scalp.

Further, said composition can be a composition for preventing, alleviating or treating urticaria, rash, tinea corporis, tinea cruris, or tinea pedis, due to mycotic infection.

Said strain, and cultures of said strain, lysates of said strain, and extracts of said strain can be comprised in an amount of 0.1% by weight to 50% by weight, based on the total weight of the composition.

Said anti-fungal composition may be a pharmaceutical composition, a cosmetic composition or a health food composition, and it can also be a skin external preparation.

Said cosmetic composition can be provided in all dosage forms which are suitable for topical application, for example, in the form of liquid, oil-in-water type emulsion, water-in-oil type emulsion, suspension, solid, gel, powder, paste, foam or aerosol. Said compositions of the above dosage forms can be prepared in conventional methods used in the art.

In addition to the above ingredients, said composition may comprise other ingredients at an amount which does not harm the main effect, preferably, at an amount to provide a synergistic effect on the main effect. The composition according to the present invention may comprise a substance selected from the group consisting of vitamins, polypeptides, polysaccharides, and sphingolipid. Further, the cosmetic composition of the present invention may comprise a moisturizer, an emollient agent, a surfactant, a UV absorbent, a preservative, a sterilizer, an antioxidant, a pH adjusting agent, organic and inorganic pigments, flavoring agent, a cooling agent or an antiperspirant agent. The combination percentage of said ingredients can be selected by those skilled in the art within the range not to hinder the purpose and effect of the present invention, and can be in a range from 0.01% by weight to 5% by weight, and specifically from 0.01% by weight to 3% by weight, based on the total weight of the composition.

According to the above embodiment, the anti-fungal composition of the present invention can be a skin external preparation such as cream, ointment, shampoo, or treatment.

According to another embodiment of the present invention, the present invention relates to a pharmaceutical composition for the treatment or prevention of allergic diseases including atopic dermatitis, inflammatory diseases, intestinal diseases and/or autoimmune diseases, comprising at least one selected from the group consisting of cellular component of *Lactobacillus gasseri* KBL697 strain, cultures of said strain, lysates of said strain, and extracts of said strain.

The pharmaceutical composition of the present invention can be provided in a form of cellular component of live bacteria, dry strain, cultures of said strain, lysates of said strain, or a composition in combination with a pharmaceutically acceptable carrier or media. The carriers or media that can be used herein may include solvent, a dispersant, a coating, an enhancer, a controlled-release formulation (i.e., sustained-release formulation), or at least one inert excipient including starch, polyol, granules, microtine cellulose, microcrystalline cellulose such as Celphere, Celphere beads, diluent, lubricant, binder, disintegrant. The tablet of the above composition may be, if desired, coated by a standard aqueous or non-aqueous technique. The examples of the pharmaceutically acceptable carrier and the excipient for the use as the pharmaceutically acceptable inert carrier, and said additional ingredients may include, for example, a binder, a filler, a disintegrant, a lubricant, an antimicrobial agent and a coating agent, but not limited thereto.

Further, the pharmaceutical composition of the present invention can be used as an external preparation comprising a dosage form selected from the group consisting of ointments, creams, pastes, liquids and solutions for cutaneous application, glycerogelatins, liniments, powders for cutaneous application, aerosols, and plasters.

In the present invention, said allergic diseases refer to the conditions associated with IL-4 or IL-5 expressions, and may include, for example, eczema, allergic asthma, atopic dermatitis, allergic rhinitis, allergic conjunctivitis, urticaria, or anaphylaxis. Preferably, the present invention may be characterized in that the diseases are selected from the group consisting of infant eczema, allergic asthma, allergic rhinitis, atopic dermatitis, allergic conjunctivitis, and food allergy, but not limited thereto.

The present invention may be characterized in that said intestinal diseases are selected from the group consisting of abdominal bloating, abdominal discomfort, infectious diarrhea caused by pathogenic microorganisms, gastrocolitis, inflammatory bowel diseases, neurogenical intestinitis syndrome, irritable bowel syndrome, overgrowth of small intestinal microorganisms and intestinal feeding diarrhea, and the diseases also include those caused by damage of barrier function of intestine.

The inflammatory bowel disease (IBD) may include Crohn's disease, the intestinal lesion accompanying with Behcet's disease, ulcerative colitis, hemorrhagic rectal ulcer, and pouchitis, and refers to a group of diseases including Crohn's disease and ulcerative colitis. Ulcerative colitis only affects the large intestine. Inflammation and ulcer of ulcerative colitis are limited to the two innermost layers, mucosa and submucosa out of four layers of the large intestine. Inflammation and ulcer of Crohn's disease can be spread throughout all layers of the intestinal wall in both small and large intestines.

Meanwhile, the irritable bowel syndrome is a chronic condition accompanying not only persistently recurrent abdominal discomfort and pain such as abdominal bloating, but also changes in bowel habit such as diarrhea and constipation. The symptoms may be exacerbated by psychological factors or stressful social circumstances.

In the present invention, the inflammatory diseases collectively refer to conditions having inflammation as a main lesion, and may include, for example, edema, conjunctivitis, periodontitis, rhinitis, otitis media, chronic sinusitis, pharyngolaryngitis, tonsillitis, bronchitis, pneumonia, gastric ulcer, gastritis, colitis, gout, eczema, acne, atopic dermatitis, contact dermatitis, seborrheic dermatitis, ankylosing spondylitis, rheumatic fever, fibromyalgia, osteoarthritis, psoriatic arthritis, rheumatoid arthritis, peri-arthritis of the shoulder, tendinitis, tenosynovitis myositis, hepatitis, cystitis, nephritis, Sjogren's syndrome, myasthenia gravis, sepsis, vasculitis, bursitis, temporal arteritis, and multiple sclerosis, but not limited thereto.

In the present invention, autoimmune diseases and the symptoms that can be alleviated by the immunoregulatory effect may include, for example, rheumatoid arthritis, lupus, systemic scleroderma, atopic dermatitis, psoriasis, psoriatic arthritis, asthma, Guilian-Barre syndrome, myasthenia gravis, dermatomyositis, polymyositis, multiple sclerosis, autoimmune encephalomyelitis, polyarteritis nodosa, Hashimoto's thyroiditis, multiple sclerosis, temporal arteritis, juvenile diabetes, alopecia areata, pemphigus, aphthous stomatitis, autoimmune hemolytic anemia, Wegener's granulomatosis, Sjogren's syndrome, Addison's disease, Crohn's disease, and Behcet's disease, but not limited thereto.

The present invention may be characterized in that the effects resulting from the strain of the present invention for immunoregulation, or for alleviating, treating or preventing autoimmune diseases or inflammatory diseases can be induced by at least one mechanism selected from increase and decrease of cytokines associated with inhibition of inflammation and immunoregulation, specifically decrease of TNF-α, IFN-γ, and IL-17 secretion and increase of IL-10 secretion.

TNF-α (tumor necrosis factor-α) is a 17 kDa peptide produced by macrophages and various other cells activated during the host immune reaction to bacterial infections and oncologic diseases. This cytokine is also known as an important mediator of immune and inflammatory reactions, and also known as a proinflammatory cytokine which plays an important role in autoimmune diseases and inflammatory diseases such as rheumatoid arthritis (RA), psoriatic arthritis, Crohn's disease, psoriasis, and ankylosing spondylitis (AS).

On the other hand, $CD4^+$ T cells can be classified into subtypes such as Th1 (T helper type 1), Th2 (T helper type 2), $CD4^+$ $CD25^+$ immunoregulatory T cell and Th17 cells (T helper 17 cell) depending on the expression of specific cytokines and transcription factors. Among those, IL-17 produced by Th17 cells is known as mostly involved in autoimmune diseases, allergic reactions, or host defense against bacterial or fungal infection.

Further, IL-10 is a peptide of 35-40 kDa produced by helper T cell, B cell, monocyte, and other cells, and has immunosuppressive and anti-inflammatory properties, for example, inhibition of production of cytokines including TNF-α, and IFN-γ.

The term 'treating', unless mentioned otherwise, refers to reversing or alleviating the diseases or conditions used with said term or one or more symptoms thereof, inhibiting the progression of the same or preventing the same. The term 'treatment' as used in the present invention refers to an act of 'treating' as defined above. Accordingly, treatment or therapeutic regimen of a disease in mammals may include one or more of the following:

(1) Inhibit the growth of the disease, that is, inhibit its development
(2) Prevent the spread of the disease
(3) Alleviate the disease
(4) Prevent recurrence of the disease, and
(5) Palliate the symptoms of the disease A composition of the present invention for preventing or treating allergic diseases such as atopic dermatitis, inflammatory diseases, intestinal diseases and/or autoimmune diseases may comprise a pharmaceutically effective amount of *Lactobacillus gasseri* KBL697 strain alone or in combination of with at least one of pharmaceutically acceptable carriers, excipients or diluents.

In the present invention, the term "effective amount" means an amount that is high enough to provide a desired effect but is low enough to prevent serious side effects under medical judgment. The amount of microorganisms administered to the body by the composition of the present invention can be appropriately adjusted in consideration of the administration route and the administration target.

The composition of the present invention can be administered to a subject once or more per day. Unit dosage means physically discrete units suitable for unit administration to human subjects and other mammals, and each unit comprises a suitable pharmaceutical carrier and a predetermined amount of *Lactobacillus gasseri* KBL697 strain of the present invention to provide a therapeutic effect. The dosage unit for oral administration to an adult patient preferably contains 0.001 g or more of the microorganism of the present invention, and the oral dosage of the composition of the present invention is from 0.001 g to 10 g, and preferably from 0.01 g to 5 g per dose. The pharmaceutically effective amount of the microorganism of the present invention is from 0.01 g to 10 g/day. However, the dosage varies depending on the severity of the patient's disease and the microorganisms and auxiliary effective ingredients used together. In addition, the total daily dosage can be divided into several times and continuously administered as needed. Accordingly, the above dosage ranges do not limit the scope of the present invention in any way.

Further, the term "pharmaceutically acceptable" as used above refers to a composition that is physiologically acceptable and does not cause an allergic reaction such as gastrointestinal disorder, or dizziness, or similar reaction when administered to a human.

A composition of the present invention can be formulated using methods known in the art so that rapid, sustained or delayed release of the active ingredients, after administered to a mammal, can be provided. The dosage forms may be powders, granules, tablets, emulsions, syrups, aerosols, soft or hard gelatin capsules, sterile injection solutions, or sterile powders. Further, the composition of the present invention for preventing or treating allergic diseases such as atopic dermatitis, inflammatory diseases, intestinal diseases and/or autoimmune diseases can be administered via several routes, including oral, transdermal, subcutaneous, intravenous or intramuscular administration. The dosage of the active ingredients can be appropriately selected depending on various factors such as the route of administration, the patient's age, sex, weight, and the severity of the patient. The composition of the present invention for treating allergic diseases such as atopic dermatitis, inflammatory diseases, intestinal diseases and/or autoimmune diseases can be administered in combination with a known compound having the effect of preventing, alleviating or treating the relevant symptoms.

The pharmaceutical composition of the present invention, in particular, can be provided in an oral unit dosage form of an enteric coated formulation. The term "enteric coating", as used herein, comprises any known pharmaceutically acceptable coating which can remain in the stomach without degrading by the gastric acid and can sufficiently disintegrate in the intestinal tract to release active ingredients therein. The "enteric coating" of the present invention refers to a coating that can be maintained for 2 hours or more when an artificial gastric juice such as an HCl solution of pH 1 is contacted thereto at 36° C. to 38° C., and subsequently can degrade, preferably in an artificial intestinal juice such as a $KH_2PO_4$ buffer solution of pH 6.8 in 30 minutes.

The enteric coating of the present invention is coated on one core in an amount of from about 16 mg to 30 mg, preferably from 16 mg to 20 mg or 25 mg or less. When the thickness of the enteric coating of the present invention is 5 µm to 100 µm, and preferably 20 µm to 80 µm, satisfactory results can be obtained as an enteric coating. The material of the enteric coating can be suitably selected from known polymeric materials. Suitable polymeric materials are listed in a number of known documents (L. Lachman et al., The Theory and Practice of Industrial Pharmacy, $3^{rd}$ ed., 1986, pp. 365~373; H. Sucker et al., Pharmazeutische Technologie, Thieme, 1991, pp. 355-359; Hagers Handbuchder pharmazeutischen Praxis, $4^{th}$ ed., Vol. 7, pp. 739~742, and 766~778, (SpringerVerlag, 1971); and Remington's Pharmaceutical Sciences, $13^{th}$ ed., pp. 1689~1691 (Mack Publ., Co., 1970)), and cellulose ester derivatives, cellulose ethers, a copolymer of acrylic resin and methylacrylate, and a copolymer of maleic acid and phthalic acid derivatives can be included therein.

The enteric coating of the present invention can be prepared using a conventional enteric coating method in which an enteric coating solution is sprayed onto a core. Suitable solvents used for the enteric coating process are alcohols such as ethanol, ketones such as acetone, halogenated hydrocarbon solvents such as dichloromethane ($CH_2Cl_2$), and mixed solvents of these solvents. A softener such as di-n-butyl phthalate or triacetin is added to the coating solution in a ratio of 1:about 0.05 to about 0.3 (coating material:softener). It is appropriate to carry out the spraying process continuously, and it is possible to adjust the spraying amount in consideration of the conditions of coating. The spraying pressure can be variously adjusted, and satisfactory results can be obtained generally with a spraying pressure of about 1 bar to about 1.5 bar.

Meanwhile, the pharmaceutical composition of the present invention can be administered in combination with conventional drugs which are known to have preventing or treating effect on allergic diseases, inflammatory diseases, intestinal diseases and/or autoimmune diseases. For example, the drugs that can be administered in combination with the pharmaceutical composition of the present invention may include antibody medications used for treating inflammatory diseases, intestinal diseases or autoimmune diseases such as infliximab, adalimumab, golimumab, abciximab, alemtuzumab, atlizumab, basiliximab, belimumab, bevacizumab, ipilimumab, brentuximab vecotin, canakinumab, capromab pendetide, catumaxomab, certolizumab pegol, cetuximab, daclizumab, denosumab, eculizumab, edrecolomab, efalizumab, efungumab, ertumaxomab, etanercept, etaracizumab, fontolizumab, gemtuzumab ozogamicin, girentuximab, ibritumomab tiuxetan, igovomab, imciromab, ipilimumab, labetuzumab, mepolizumab, motavizumab, natalizumab, nimotuzumab, nofetumomab merpentan, ofatumumab, omalizumab, oregovomab, palivizumab, panitumumab, pemtumomab, pertuzumab, ranibizumab, raxibacumab, rituximab, rovelizumab, ruplizumab, tacatuzumab tetraxetan, tefibazumab, tocilizumab, tositumomab, trastuzumab, ustekinumab, secukinumab, vedolizumab, visilizumab, votumumab, zalutumumab and zanolimumab, but not limited thereto.

In addition, the pharmaceutical composition of the present invention can be used in combination with antihistamines, steroids, salicylic acid, urea, tacrolimus, cyclophosphorine, phototherapy, and the like, for the treatment of eczema and allergic diseases such as atopic dermatitis, and can be used in combination with sulfasalazine, azathioprine, mercaptopurine, methotrexate, cyclosporine, TNF blocking agents (adalimumab, etanercept, etc.), or integrin antibodies (vedolizumab, natalizumab, etc.), for the treatment of intestinal diseases such as inflammatory bowel diseases.

In another embodiment of the present invention, the present invention provides the use of said strain or said composition for preventing or treating allergic diseases such as atopic dermatitis, inflammatory diseases, intestinal diseases and/or autoimmune diseases, and the use of said strain or said composition for preparing a therapeutic agent for the above diseases.

Specifically, the present invention relates to a composition comprising at least one selected from the group consisting of said strain, cultures of said strain, lysates of said strain, and extracts of said strain, for the use of preventing or treating allergic diseases including atopic dermatitis, inflammatory diseases, intestinal diseases such as colitis, and/or autoimmune diseases such as psoriasis.

The present invention also relates to the use of a composition for preparing a preventive or therapeutic drug for allergic diseases including atopic dermatitis, inflammatory diseases, intestinal diseases such as colitis, and/or autoimmune diseases such as psoriasis, comprising at least one selected from the group consisting of said strain, cultures of said strain, lysates of said strain, and extracts of said strain.

The term 'prevention', as used herein, is associated with averting, delaying, impeding or hindering diseases to reduce the same.

The term 'treatment', as used herein, is associated with caring for a subject suffering from diseases in order to ameliorate, cure or reduce the symptoms of the diseases or to reduce or stop the progression of the diseases.

In another embodiment of the present invention, the present invention provides a method for preventing or treating allergic diseases including atopic dermatitis, inflammatory diseases, intestinal diseases and/or autoimmune diseases, comprising administering a pharmaceutically effective amount of the strain or said composition to a subject in need of prevention or treatment of said diseases, or in need of alleviation of the intestinal health, allergic reactions, inflammatory reactions or autoimmunity reactions.

Specifically, the present invention provides a method for treating allergic diseases including atopic dermatitis, inflammatory diseases, intestinal diseases such as colitis, and/or autoimmune diseases such as psoriasis, comprising administering a therapeutically effective amount of at least one selected from the group consisting of said strain, cultures of said strain, lysates of said strain, and extracts of said strain to a subject in need thereof.

Since the pharmaceutical composition used for the method for preventing or treating said diseases, and the administration method thereof have been described above, the overlapping contents between the composition and the method will be omitted herein to avoid excessive complexity of the present specification.

Meanwhile, the said subject to which the composition for preventing or treating said diseases can be administered includes all animals including human. For example, the subject may be an animal such as dog, cat, or mouse.

In another embodiment of the present invention, the present invention relates to a cosmetic composition comprising a pharmaceutically effective amount of at least one selected from the group consisting of the cellular component of *Lactobacillus gasseri* KBL697 strain, cultures of said strain, lysates of said strain, and extracts of said strain.

The cosmetic composition may be characterized by its function of alleviating at least one sensitive skin condition selected from the group consisting of cutaneous allergy, skin urticaria, atopic dermatitis, psoriasis, mycotic infections and eczema, but not limited thereto.

The term 'cosmetic composition', as used herein, refers to a composition comprising at least one selected from the group consisting of the cellular component of *Lactobacillus gasseri* KBL697 strain, cultures of said strain, lysates of said strain, and extracts of said strain, and may take any type of dosage form. For example, the cosmetics prepared by using the said cosmetic composition may include creams, packs, lotions, essences, toners, foundations and makeup bases, and may be commercialized in any dosage forms listed above to achieve the purpose of the present invention, but not limited thereto. The ingredients comprised in the cosmetic composition of the present invention include those commonly used in cosmetic compositions, in addition to the above ingredients, for example, conventional adjuvants such as antioxidants, stabilizers, solubilizers, vitamins, pigments and fragrances, and carriers.

In another embodiment of the present invention, the present invention relates to a functional patch comprising at least one selected from the group consisting of the cellular component of *Lactobacillus gasseri* KBL697 strain, cultures of said strain, lysates of said strain, and extracts of said strain, and said functional patch may be used for cosmetic or medical purpose.

The patch may be characterized by its function of alleviating at least one sensitive skin condition selected from the group consisting of cutaneous allergy, skin urticaria, atopic dermatitis, psoriasis, mycotic infections and eczema, but not limited thereto.

In the present invention, the patch is typically a small adhesive bandage containing the substances to be delivered, and the bandage can take a variety of forms. The simplest form is an adhesive single body comprising a reservoir containing the substances to be delivered placed on a support. The reservoir is typically formed from a cosmetically or pharmaceutically acceptable pressure sensitive adhesive, but in some cases may also be formed from non-adhesive materials provided with a thin adhesive layer suitable for the skin contacting surface. The rate at which the substances to be delivered are administered from the patch to the subject wearing the patch can be changed because the permeability of the skin to the substances to be delivered usually depends on individuals and the location of the skin, which can be easily selected by those skilled in the art.

Hereinafter, the present invention will be described in more detail through examples. These examples are only for illustrating the present invention, and it will be apparent to those skilled in the art that the scope of the present invention is not to be construed as being limited by these examples.

[16] Example 1. Alleviation and Therapeutic Effects by KBL697 for Allergic Reactions Resulting from Inhibition of Th2 Type Cytokines in T Cells Type-2 helper T cell (Th2)-related cytokines, such as IL-4 and IL-5, have been reported to contribute to chronic allergic reactions by increasing Th2-related immune reactions and increasing IgE production (Passante E, *Inflamm. Res.* 2009). The present invention, by verifying the effect of inhibiting IL-4 and IL-5 secretion by various *Lactobacillus* strains, attempted to screen probiotic strains that can be used as therapeutic agents for various allergic diseases including chronic allergic diseases. To this end, the effect of inhibiting the secretion of IL-4 and IL-5 was tested as follows, using EL4 cell line which is the mouse T cell line.

[17] 1-1. Incubation of EL-4 Cell Lines

EL4 (ATCC NO. TIB-39) cells were cultured in DMEM medium supplemented with 10% FBS (fetal bovine serum), penicillin (100 μg/mL), and streptomycin (100 μg/mL) at 37° C. under 5% $CO_2$, and then subcultured once every three days. EL4 cells were seeded onto a 24-well plate with a concentration of $4 \times 10^5$ cells/well, then cultured for 16 to 20 hours to induce allergic reactions, and treated with strains.

[18] 1-2 Incubation of Strains and Recovery

The *Lactobacillus gasseri* strains to be used were cultured in MRS medium supplemented with 0.5% cysteine, were activated through a total of two subcultures at 18-hour intervals, and then were used in experiments. The resulting culture solution was centrifuged at 15,000×g for 3 minutes, and the pellet was washed with a PBS buffer. The strains were stained for 15 minutes with SYTO9 and PI by using LIVE/DEAD™ BacLight™ Bacterial Viability and Counting Kit for flow cytometry (Thermo Fisher Scientific, USA). Then, the contained beads were added, and the number of stained live bacteria was calculated by using a flow cytometry assay.

1-3. Strain Treatment and Measurement of an Amount of IL-4 and IL-5 Secretion after Inducing Allergic Reactions In order to induce allergic reactions in the EL4 cells previously seeded onto a 24 well plate, each well was treated with 100 μL of PMA (20 ng/mL) and ionomycin (1 μg/mL). Then, 300 μL of the previously prepared strains was treated in the ratio of cell to strain of 1:10. After incubation for 24 hours in the 5% $CO_2$ incubator at 37° C., the supernatant was collected, and Mouse IL-4 ELISA set (Cat NO. 555232, BD OptEIA™) and Mouse IL-5 ELISA set (Cat NO. 555236, BD OptEIA™) were used to measure the amount of IL-4 and IL-5 secreted, according to the manufacturer's method.

Figure 2:
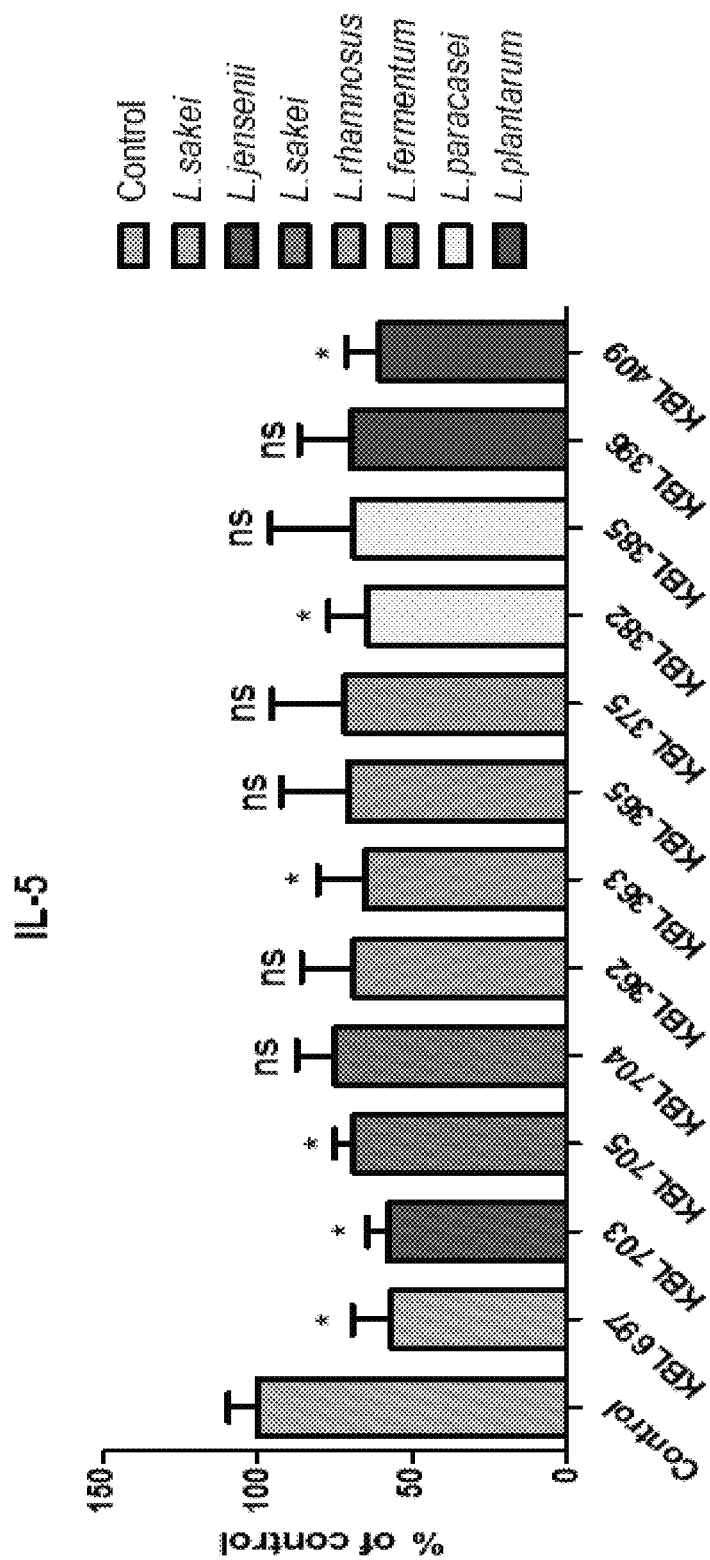
FIG. 2 illustrates the result confirming the inhibitory effect of IL-5 expression by various Lactobacillus strains including Lactobacillus gasseri KBL697 strain, after inducing allergic reaction in EL4 cell lines.

As a result, as shown in FIGS. 1 and 2, it was confirmed that KBL697 effectively inhibited the secretion of both IL-4 and IL-5, and therapeutic and preventive effects thereof on allergies could be provided through inhibition of secretion of Th2 type cytokine that mediates an allergic reaction.

Example 2. Alleviation and Treatment Effects by KBL697 for Allergic Reactions Resulting from Inhibition of Histamine Secretion in Basophils It has been reported that, in an allergic reaction, histamine is expressed in tissues, causing an inflammatory reaction, and suppressing histamine secretion leads to alleviation of allergic symptoms by blocking the reaction by histamine. In the present invention, the alleviation of allergic reactions and the therapeutic effect thereon through inhibition of histamine secretion by KBL697 were further confirmed. Further, in order to confirm whether the effect for treating and preventing chronic allergies identified in Example 1 is an inherent attribute of *Lactobacillus gasseri*, or is a remarkable effect particularly in KBL697 among *Lactobacillus gasseri*, the ability to suppress histamine secretion was evaluated also for nine additional *Lactobacillus gasseri* strains in addition to KBL697. After inducing degranulation after culturing the RBL-2H3 cell line, the ability to suppress histamine secretion was tested by measuring the activity of β-hexosaminidase co-secreted with histamine using a colorimetric reaction with a substrate.

2-1. Incubation of RBL-2113 Cell Lines

RBL-2H3 (ATCC NO. CRL-2256) cells were cultured in DMEM medium supplemented with 10% FBS, penicillin (100 μg/mL), and streptomycin (100 μg/mL) at 37° C. under 5% $CO_2$, and then subcultured once every three days. RBL-2H3 cells were seeded onto a 6-well plate with a concentration of $1\times10^6$ cells/well, then cultured for 3 hours, and then treated with IgE (0.5 μg/mL) to incubate for 16 to 20 hours.

2-2. Incubation of Strains and Preparation of Culture Solution

The *Lactobacillus gasseri* strains to be used were cultured in MRS medium supplemented with 0.5% cysteine, were activated through a total of two subcultures at 18-hour intervals, and then were used in experiments. The resulting culture solution was centrifuged at 15,000×g for 3 minutes to collect the supernatant.

2-3. Inducing Degranulation after Treatment of Strains

After removing the medium of RBL-2H3 cells which were previously seeded onto a 6-well plate, the cells were washed twice with 1 mL of Siraganian buffer (pH 7.2). Thereafter, the cells were treated with 120 μL of the previously prepared bacterial culture solution or the positive control group ketotifen (20 μg/mL) per well, incubated for 20 minutes in the 5% $CO_2$ incubator at 37° C., followed by treating with 60 μL of antigen (DNP-HAS, 1 μg/mL) to induce degranulation by the antigen-antibody reaction. As a negative control, degranulation was induced after treating with 120 μL of the Siraganian buffer. The reaction was carried out in the 5% $CO_2$ incubator at 37° C. for 20 minutes, and then the supernatant was collected.

2-4. Identification of Color Reaction

To identify the activity of β-hexosaminidase, 25 μL of the supernatant collected in Example 2-3 was transferred to each well of a 96-well plate, and then 25 μL of substrate (p-nitrophenyl N-acetyl-D-glucosaminidase) was added to each, and followed by a reaction at 37° C. in the 5% $CO_2$ incubator for 90 minutes. Then, 200 μL of stop solution ($Na_2CO_3$/$NaHCO_3$) was added to stop the reaction and then absorbance was measured at 405 nm. The absorbance when treated with each type of *Lactobacillus gasseri* was compared to the negative control group and converted to percentage to show the level of inhibition of the degranulation.

Figure 3:
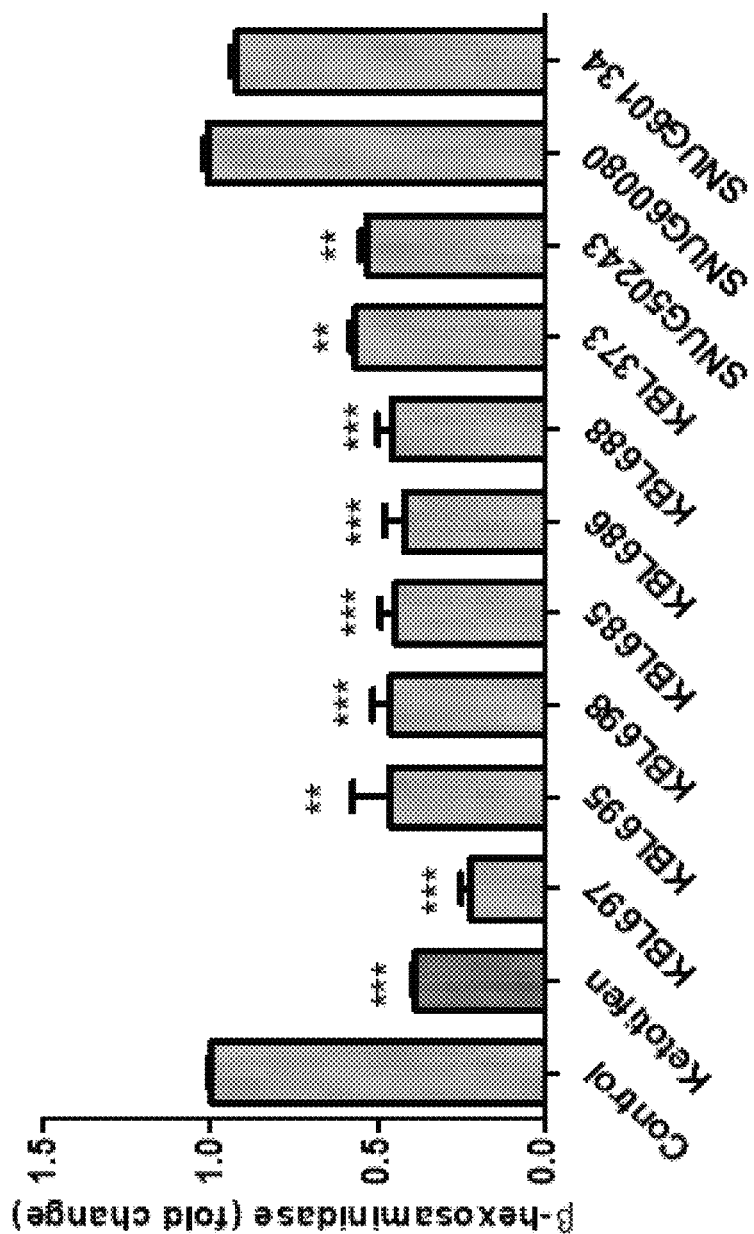
FIG. 3 illustrates the result confirming an inhibitory effect of histamine secretion by the treatment of various Lactobacillus gasseri strains, and an antihistaminic agent ketotifen, after inducing histamine production by antigen-antibody reaction in RBL 2H3 cell lines.

As a result, as can be seen in FIG. 3 and Table 1, KBL697 showed up to 4 times lower amount of β-hexosaminidase secretion compared to other *Lactobacillus gasseri* strains, which was confirmed to be lower than that of the commercially available antihistamine agent ketotifen, a positive control. As a result, it was found that KBL697 exhibited excellent degranulation-preventing activity to effectively alleviate allergic symptoms caused by excessive secretion of histamine.

TABLE 1

| Species | Strain under Treatment or Treatment Drug | β-hexosaminidase (fold change) |
|---|---|---|
| - (Negative control) | Siraganian buffer | 1.0 |
| - (Positive control) | Ketotifen | 0.3861 |
| *Lactobacillus gasseri* | KBL697 | 0.2213 |
| *Lactobacillus gasseri* | KBL695 | 0.4601 |
| *Lactobacillus gasseri* | KBL698 | 0.4620 |
| *Lactobacillus gasseri* | KBL685 | 0.4450 |
| *Lactobacillus gasseri* | KBL686 | 0.4213 |
| *Lactobacillus gasseri* | KBL688 | 0.4571 |
| *Lactobacillus gasseri* | KBL373 | 0.5691 |
| *Lactobacillus gasseri* | SNUG50243 | 0.5309 |
| *Lactobacillus gasseri* | SNUG60080 | 1.0091 |
| *Lactobacillus gasseri* | SNUG60134 | 0.9236 |

Example 3. Analysis of Immunoregulatory and Inflammation Inhibitory Effects of KBL697

Immunoregulatory and inflammatory inhibitory effects of KBL697 were also verified in addition to the anti-allergic efficacy thereof. To this end, the ratio between IL-10, a representative cytokine that has an immunomodulatory function, and TNF-α and IL-6, which are cytokines as the major indicators of an inflammatory reaction (IL-10/TNF-α, IL-10/IL-6) was measured by using macrophage, which plays a critical role in the inflammatory reaction.

3-1. Incubation of RAW264.7 Cell Lines

RAW264.7 (ATCC NO. TIB-71) cells were cultured in DMEM medium supplemented with 10% FBS, penicillin (100 m/mL), and streptomycin (100 m/mL) at 37° C. under 5% $CO_2$, and then subcultured once every three days. RAW264.7 cells as incubated were seeded onto a 24-well plate with the concentration of 1×10$^5$ cells/well, then cultured for 16 to 20 hours, and then used for Example 3-3.

3-2. Incubation of Strains and Preparation of Samples

The culture solutions were corrected with the same number of live bacteria and then prepared as three samples: live bacteria, pasteurization and heat killing. The samples for live bacteria, pasteurization and heat killing were prepared according to the same method as that of Example 1-2. Then, the sample for pasteurization was reacted at 70° C. for 30 minutes and prepared through the same centrifugation process. The sample of heat killing was sterilized at 121° C. for 15 minutes and prepared through the same process. As a negative control group, the MRS medium supplemented with 0.5% cysteine was used.

3-3. Strain Treatment and Measurement of an Amount of Inflammatory Cytokines Secreted After Inducing Inflammatory Reactions In order to induce inflammatory reactions in RAW264.7 cells previously seeded onto a 24-well plate, each well was treated with 500 μL of LPS (20 ng/mL). Then, 300 μL of the previously prepared strains was treated in the ratio of cell to strain of 1:10, and incubated for 24 hours in the 5% $CO_2$ incubator at 37° C. The supernatant in the cultured cell-strain mixture was collected and Mouse TNF ELISA Set II (Cat No. 558534, BD OptEIA™), Mouse IL-6 ELISA Set (Cat No. 555240, BD OptEIA™), and Mouse IL-10 ELISA Set (Cat No. 555252, BD OptEIA™) were used to measure an amount of each cytokine, according to the manufacturer's method.

Figure 4:
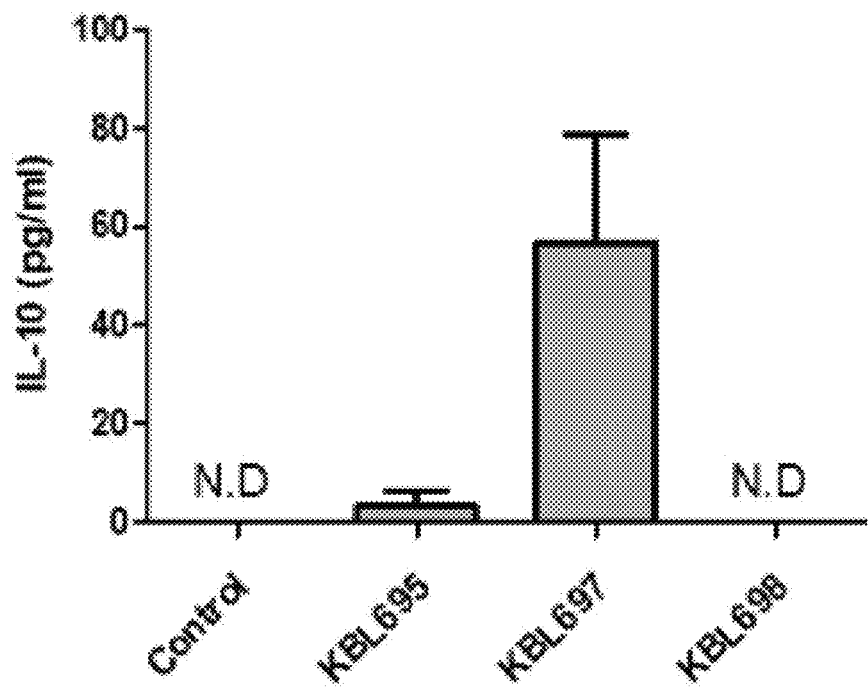
FIG. 4 illustrates the result of observation of the remarkable effect of increasing the amount of anti-inflammatory, immunoregulatory cytokine IL-10 secretion by the treatment of the KBL697 strain, when treating with Lactobacillus gasseri strains after inducing inflammatory reaction in RAW 264.7 cell lines.
Figure 5:
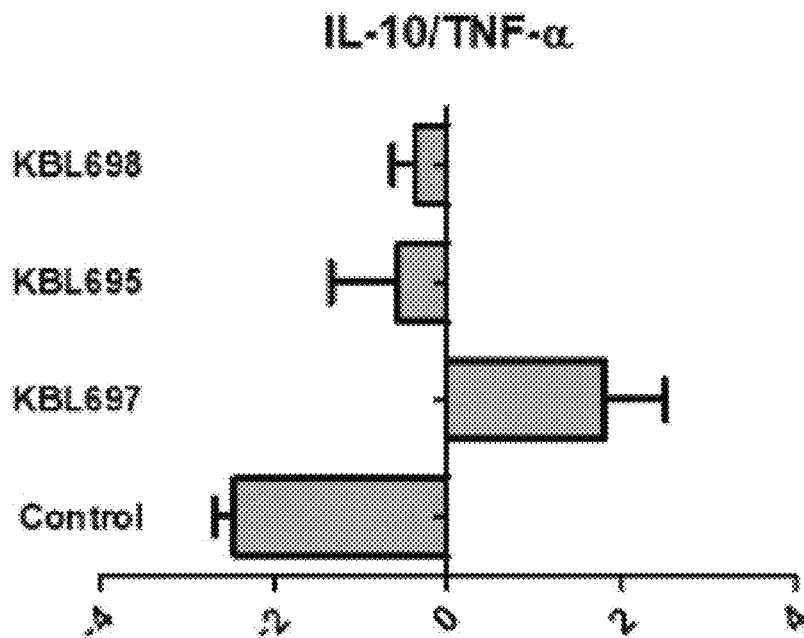
FIG. 5 illustrates the result confirming the remarkable immunoregulatory and anti-inflammatory effect by the treatment of the KBL697 strain with an IL-10/TNF-α value, when treating with Lactobacillus gasseri strains after inducing inflammatory reaction in RAW 264.7 cell lines.
Figure 6:
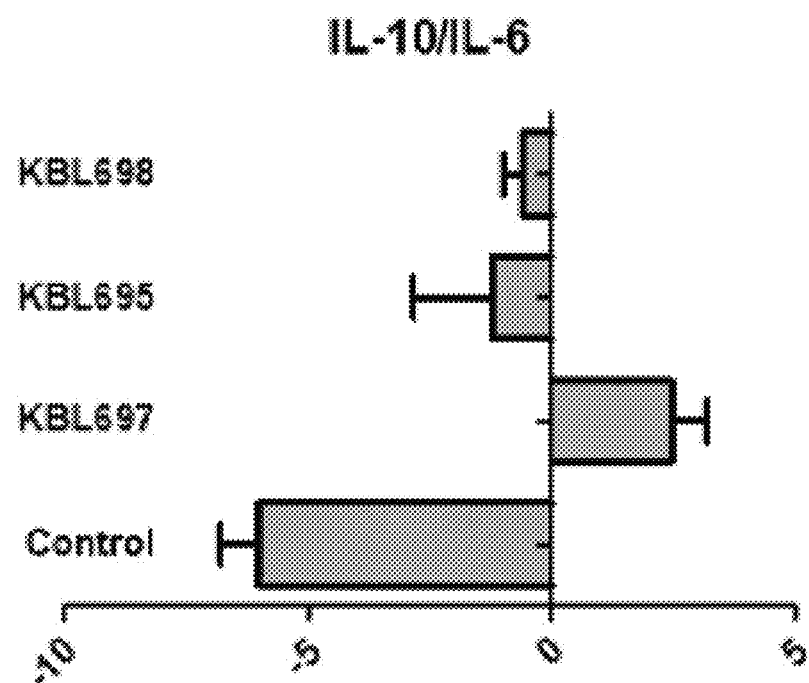
FIG. 6 illustrates the result confirming the remarkable immunoregulatory and anti-inflammatory effect by the treatment of the KBL697 strain with an IL-10/IL-6 value, when treating with the *Lactobacillus gasseri* strains after inducing inflammatory responses in RAW 264.7 cell lines.

As a result, as shown in FIG. 4, it was confirmed that especially KBL697, among *Lactobacillus gasseri* strains, induced IL-10 secretion and thus showed excellent effects in terms of immunoregulation and inflammatory reaction suppression. As shown in FIGS. 5 and 6, from the ability to secrete IL-10 corrected with the pro-inflammatory cytokines TNF-α and IL-6, it was confirmed that the KBL697 treatment group showed the inflammation inhibitory effect and immunoregulatory ability much enhanced compared to the control group. Accordingly, it has been found that KBL697 has immunoregulatory and inflammation inhibitory activities through IL-10 secretion. In addition, these effects were similarly confirmed not only in live bacteria but also in pasteurized or heat killed dead bodies (see Table 2 and Table 3), indicating that KBL697 can be used to suppress inflammatory reactions in various forms such as dead bacteria.

TABLE 2

| IL-10/TNF-a | Live | Heat-killed | Pasteurized |
|---|---|---|---|
| Control | −2.4509342 (N.D.) | −2.0474707 (N.D.) | −1.9242497 (N.D.) |
| KBL697 | 1.81114395 | 6.28130388 | 4.43515847 |

N.D.: Not Determined

TABLE 3

| IL-10/IL-6 | Live | Heat-killed | Pasteurized |
|---|---|---|---|
| Control | −6.010433 (N.D.) | −4.6669667 (N.D.) | −4.5960301 (N.D.) |
| KBL897 | 2.4709538 | 8.1665268 | 5.65439003 |

N.D.: Not Determined

Example 4. Analysis of Anti-Fungal Effects of KBL697

The anti-fungal effect of KBL697 was confirmed by a spot assay method. About 1% of KBL697 was inoculated on MRS liquid medium, and then was incubated in the 37° C. incubator for about 24 hours under anaerobic conditions for stationary culturing. The culture solution in which the cells were incubated was spotted in the MRS solid medium, which was prepared under anaerobic conditions, in an amount of 10 μL at each time, and then incubated at 37° C. under anaerobic conditions for about 24 hours. *Malassezia furfur* KCTC 7545, a fungal microorganism, was prepared by inoculating it in the mYPG liquid medium, which was prepared under aerobic conditions, at a rate of 1% and followed by incubation in the 37° C. incubator for about 24 to 48 hours. The mYPG soft medium to be used for anti-fungal efficacy evaluation was prepared with the components shown in Table 4, and 2.5 mL of the prepared culture medium was inoculated with the culture solution in which 500 μL of *M. furfur* was incubated. 2.5 mL of mYPG soft medium inoculated with *M. furfur* was poured into the MRS medium spotted with KBL697 and dried for 1 hour. The dried medium was incubated under aerobic conditions in the 37° C. incubator for 24 to 48 hours. When a clear zone was identified in the cultured medium, anti-fungal activity was determined by measuring the length from the outside of the spotted lactic acid bacteria to the clear zone. The clear zone is a part where growth of fungi was inhibited, and the anti-fungal activity caused by lactic acid bacteria was determined through the length to the clear zone.

Figure 7:
FIG. 7 illustrates the result of a spot assay confirming the anti-fungal activity of *Lactobacillus gasseri* KBL697 strain.

As a result of three repeated experiments, the clear zones were identified at intervals of about 6.00 mm at the part spotted with KBL697 (FIG. 7), which indicates that KBL697 can effectively suppress the growth of fungal microorganisms.

TABLE 4

| Components | Proportion (g/l) |
|---|---|
| Malt extract | 5.0 |
| Peptone | 10.0 |
| Glucose | 20.0 |
| Tween 40 | 1.0 |
| Tween 80 | 1.0 |
| Agar | 4.5 |

Example 5. Effects of KBL697 on Alleviation of Atopic Conditions

In order to verify the effect on atopic alleviation among the allergy improvement effects of KBL697, the NC/Nga mouse model, an animal model of atopic skin disease, was used.

After dividing NC/Nga mice into groups of five mice, the back of each mouse was epilated from the lower ear to the upper tail and mice were left for 24 hours. Then, 200 μL of a 1% DNCB (dinitrochlorobenzene) solution (acetone:olive oil=3:1) was applied twice a week onto the epilated portion to induce atopic dermatitis. From the third week of dermatitis induction, 200 μL of PBS was orally administered to the mice in the control group daily; the cultured KBL697 strain was centrifuged, washed through dilution with PBS and recovery, and then prepared so that at least 2×10$^9$ (KBL697-9)/2×10$^8$ (KBL697-8)/2×10$^7$ (KBL697-7) CFU could be added to 200 μL of PBS, which was orally administered to the mice in the test group in 200 μL/day. Meanwhile, 200 μL of dexamethasone (60 μg/mL) was administered to the mice in the positive control group. Then, during three weeks of administration of the bacteria, dermatitis scores of the mice in the control and test groups were measured weekly, and on the 3rd week after the administration of the bacteria, the mouse's scratching time and skin thickness, and IgE concentration-in-blood after conducting autopsies of mice were measured.

5-1. Evaluation of Dermatitis Score

To evaluate DNCB-induced skin lesions, the dermatitis score was measured through the following method. Skin conditions were monitored by taking pictures for 3 weeks at one week intervals from the 3rd week since the strain was administered. Four indicators of dryness, edema, erythema/hemorrhage, and erosion/excoriation of the skin were checked. And a condition with no lesions was scored as point 0, a mild condition as point 1, a moderate condition as point 2, and a severe condition as point 3, and the total score was evaluated.

Figure 8:
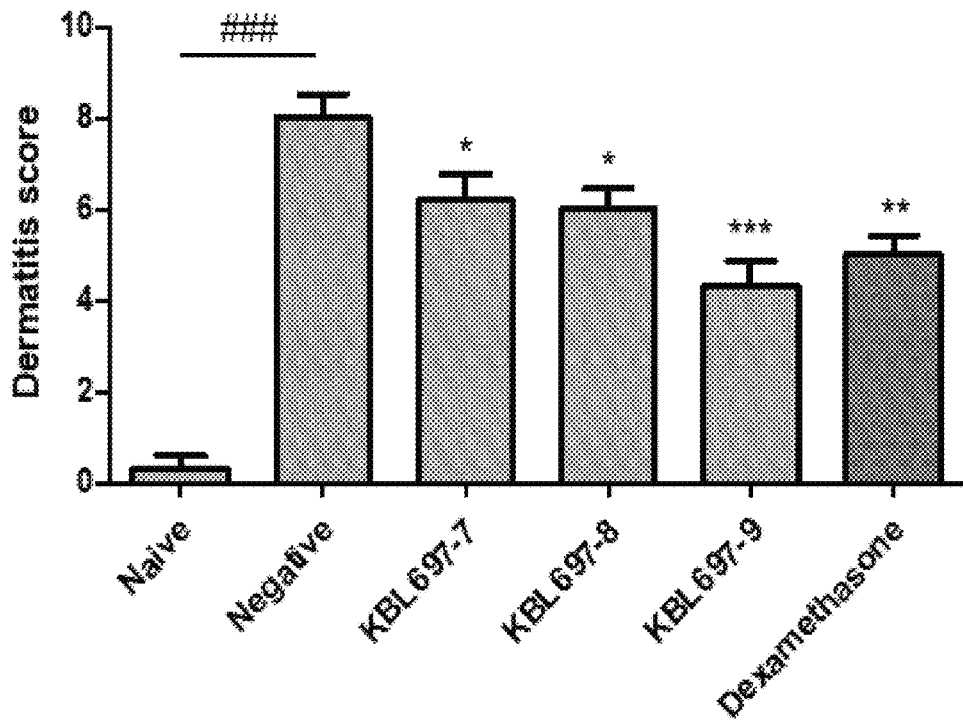
FIG. 8 illustrates the result confirming the dermatitis score reducing effect by the oral administration of *Lactobacillus gasseri* KBL697 strain to mouse models that atopic dermatitis was induced.

As a result, as shown in FIG. 8, the dermatitis score induced by DNCB was significantly reduced in the group dosed with KBL697, compared to the control group (negative) where atopic dermatitis was induced, and in particular, the test group (KBL697-9) that KBL697 was administered at $2 \times 10^9$ CFU showed the dermatitis score even lower than the positive control group of dexamethasone administration. As a result, the effect of treating atopic dermatitis according to the administration of KBL697 was verified.

5-2 Itching Relief Effects

In order to verify the effect of alleviating itching according to the administration of KBL697 in the mouse models suffering from atopic dermatitis induced by DNCB, the scratching time was measured by taking a video of the mouse models for 10 minutes after 3 weeks of strain administration.

Figure 9:
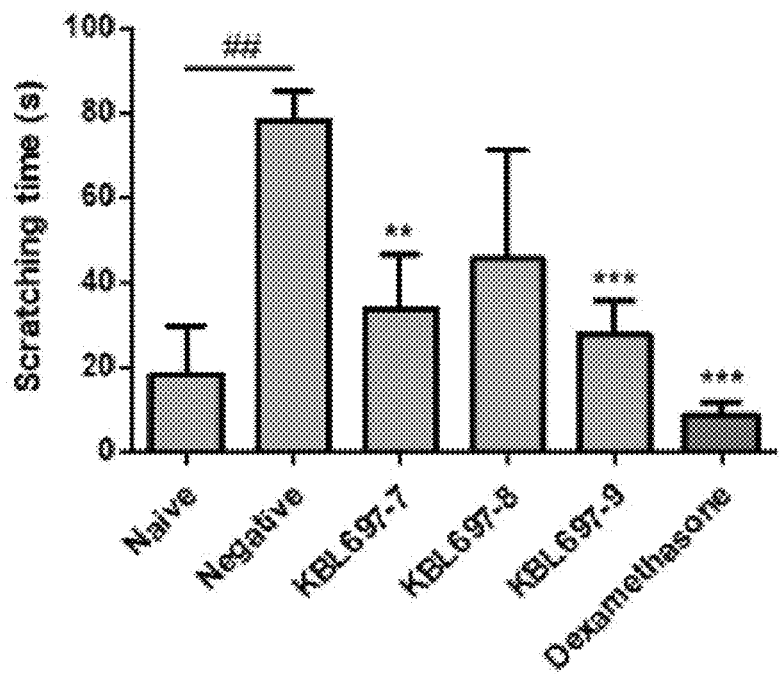
FIG. 9 illustrates the result confirming the itching-alleviating effect by the oral administration of *Lactobacillus gasseri* KBL697 strain to mouse models that atopic dermatitis was induced.

As a result, as can be seen in FIG. 9, it appeared that the scratching time was significantly reduced in all test groups that KBL697 was administered, compared to the PBS administration group, which confirmed that the itching symptoms of atopic dermatitis were much alleviated by the administration of KBL697.

5-3. Decrease of Skin Thickness

In order to verify the effect of alleviating itching after administration of KBL697 to mouse models suffering from atopic dermatitis induced by DNCB, the mouse ear thickness and dorsal skin thickness were measured with calipers three weeks after the strain was administered, and the relief of edema symptom due to atopic dermatitis was observed.

Figure 10:
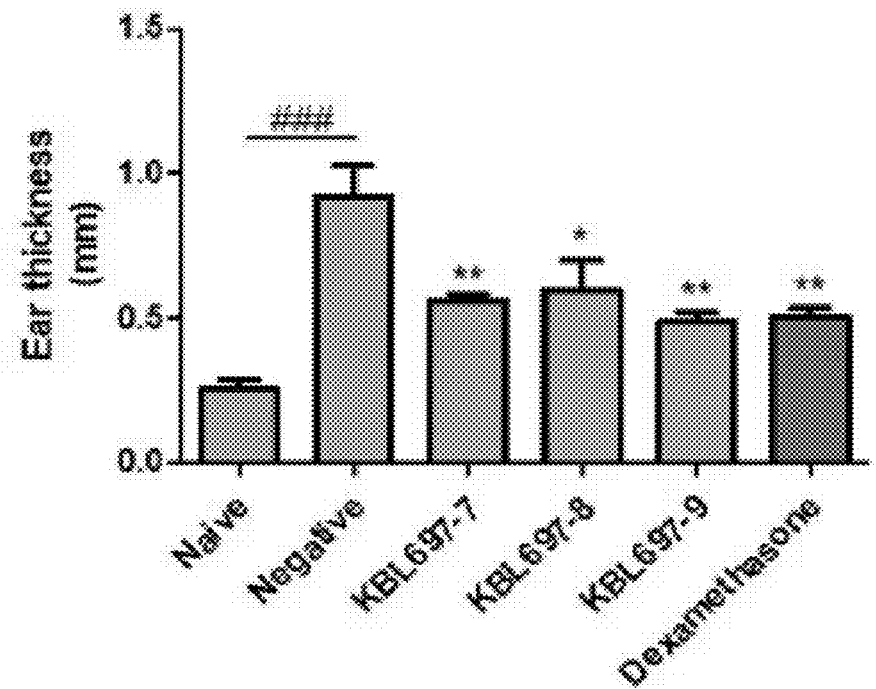
FIG. 10 illustrates the result confirming the ear thickness lowering effects by the oral administration of *Lactobacillus gasseri* KBL697 strain to mouse models that atopic dermatitis was induced.
Figure 11:
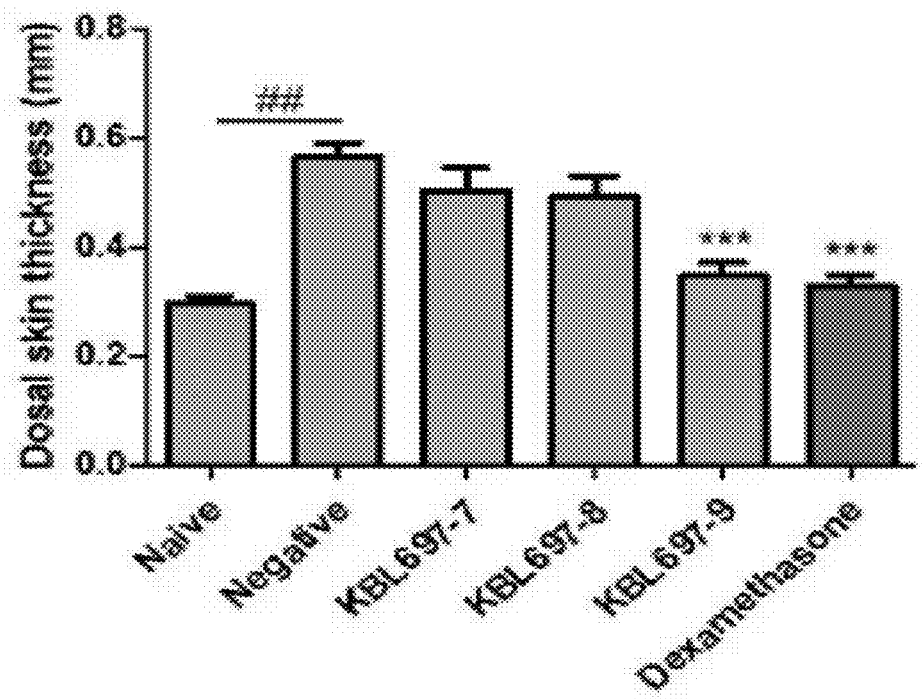
FIG. 11 illustrates the result confirming the skin thickness lowering effect by the oral administration of *Lactobacillus gasseri* KBL697 strain to mouse models that atopic dermatitis was induced.

As a result, as can be seen in FIGS. 10 and 11, it was observed that in the test group dosed with KBL697 and the positive control group, the ear and dorsal skin thicknesses were significantly reduced.

5-4. Decrease in IgE Concentration-in-Blood

It has been found that the concentration of IgE in patients having atopic dermatitis has mostly increased as clinical severity of atopic dermatitis increased (Matsumoto M, J. Immunol. 1999). Thus, the concentration of IgE, a representative hematologic factor appearing as atopic dermatitis arises, was measured by collecting blood three weeks after the strain was administered, separating serum therefrom and using Mouse IgE ELISA Set (Cat No. 555248, BD OptEIA™).

Figure 12:
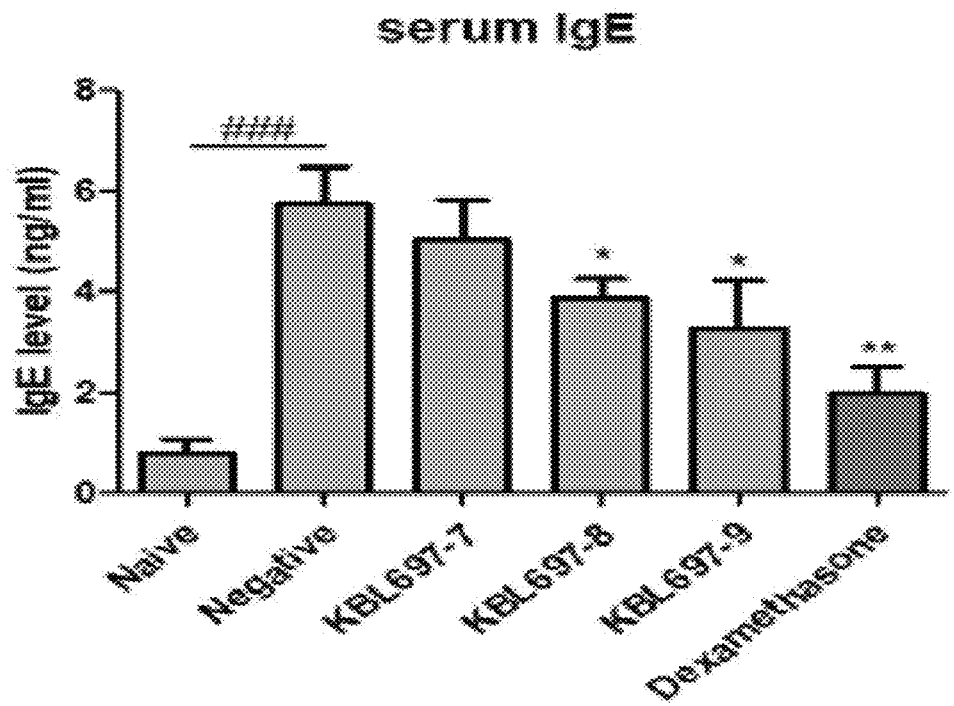
FIG. 12 illustrates the result confirming the IgE concentration-in-blood lowering effect by the oral administration of *Lactobacillus gasseri* KBL697 strain to mouse models that atopic dermatitis was induced.

As a result, as shown in FIG. 12, it was found that the concentration of IgE-in-blood was significantly decreased in the test group that KBL697 was orally administered, which indicated the anti-allergic effect after administration of KBL697.

Example 6. Effects of KBL697 on Strengthening Mesenteric Tight Junction

In the case of colitis patients, the expression of proteins involved in the tight junction of enterocytes decreases, resulting in higher cell permeability, which leads to more severe inflammatory reactions (J. Landy, *World J. Gastroenterol.*, 2016). In this regard, the present invention attempted to confirm whether KBL697 could enhance tight junction in Caco-2 cell lines, a representative intestinal epithelial cell model.

6-1. Incubation of Caco-2 Cell Lines

Caco-2 (ATCC NO. HTB-37) cells were incubated in the MEM medium supplemented with 10% FBS, penicillin (100 μg/mL), and streptomycin (100 μg/mL) at 37° C. under 5% $CO_2$, while replacing the medium once every 2 days, and then subcultured once every 4 days.

6-2. Measurement of Tight Junction

200 μL of Caco-2 cells was seeded onto the upper layer portion of the 24 Transwell plate (Corning, USA) at a concentration of $3 \times 10^5$ cells/mL, and then incubated for seven days. On the next day, after replacing the medium with that having only MEM without FBS, the cells were incubated overnight, and a chopstick electrode set was inserted thereto to measure TEER (transepithelial electrical resistance) by using EVOM Epithelial Tissue Voltohmmeter (World Precision Instruments, Florida, USA) (0 h TEER). Then, the strains were treated so that the ratio of cell to strain would be 1:100, and incubated for 24 hours, and then TEER was measured (24 h TEER).

After calculating by the equation:

TEER ($\Omega \cdot cm^2$)=(resistance ($\Omega$)−background resistance ($\Omega$))×membrane area ($cm^2$), the following equation applied:

TEER change (%)=24 h TEER ($\Omega \cdot cm^2$)/0h TEER ($\Omega \cdot cm^2$)×100

Figure 13:
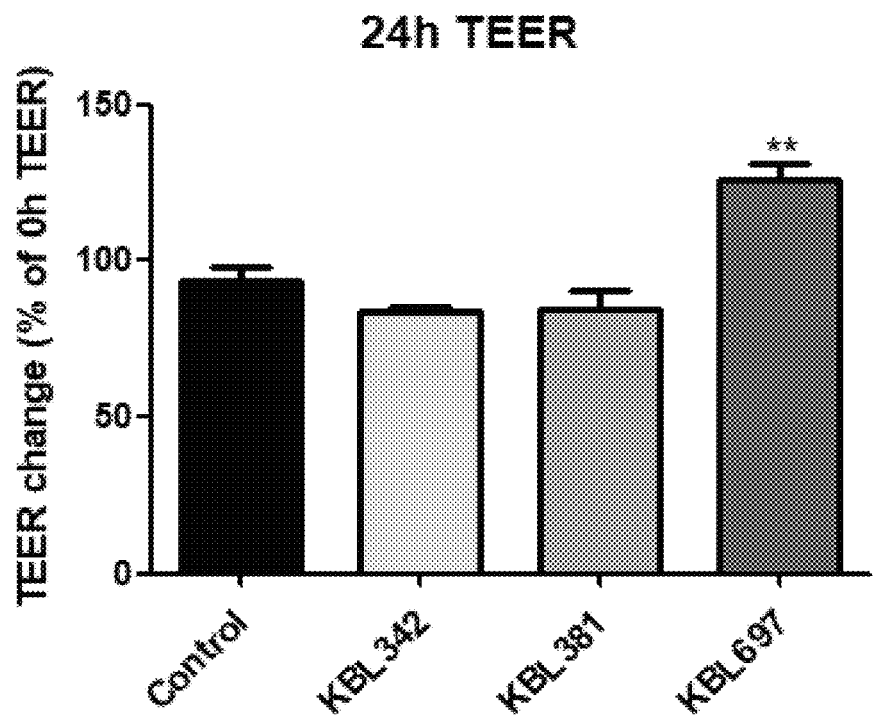
FIG. 13 illustrates the result of a TEER assay confirming the effect of strengthening tight junctions by *Lactobacillus gasseri* KBL697 strain.

As a result, as shown in FIG. 13, the Caco-2 cell lines treated with KBL697 showed that the tight junction increased by 20%, compared to the control group, indicating that KBL697 has an effect of restoring the weakened intercellular junctions between enterocytes due to colitis. On the other hand, such an effect was not found in other *Lactobacillus gasseri* strains KBL342 and KBL381.

Example 7. Effects of KBL697 on Treatment and Prevention of Colitis

In order to verify the therapeutic effect of KBL697 on colitis, mouse models in which colitis was induced were used. The mouse models were divided into groups of five C57BL/6 mice, and then fed tap water with 3% DSS dissolved therein for 5 days, and thereby inducing colitis. Subsequently, the mice in the positive control group were orally administered with the steroid-based drug prednisolone in 200 μL of PBS in accordance with 1 mg/kg/day, and the mice in the test group were daily provided via an oral administration with 200 μL of KBL697 strains which were prepared in a same manner as in Example 5 and then each diluted to be $5 \times 10^9$ CFU/mL, $5 \times 10^8$ CFU/mL, and $5 \times 10^7$ CFU/mL. The mice in the control group were orally administered with 200 μL of PBS daily. The PBS used in this example was prepared so that 0.05% of cysteine could be added to rule out the effect of small amounts of cysteine which was included in the composition of the strain culture solution and remained even after washing, according to the report that cysteine was associated with anti-inflammation in some cells (Hasegawa, S et al., Clin Exp Immunol. 2012, 167, 269-27). From the day the DSS began to be consumed until the $21^{st}$ day, the weight changes of mice in the control and test groups were measured daily, and on the $21^{st}$ day after the DSS was supplied, the mice were subjected to autopsies to measure the length of the colon.

Figure 14:
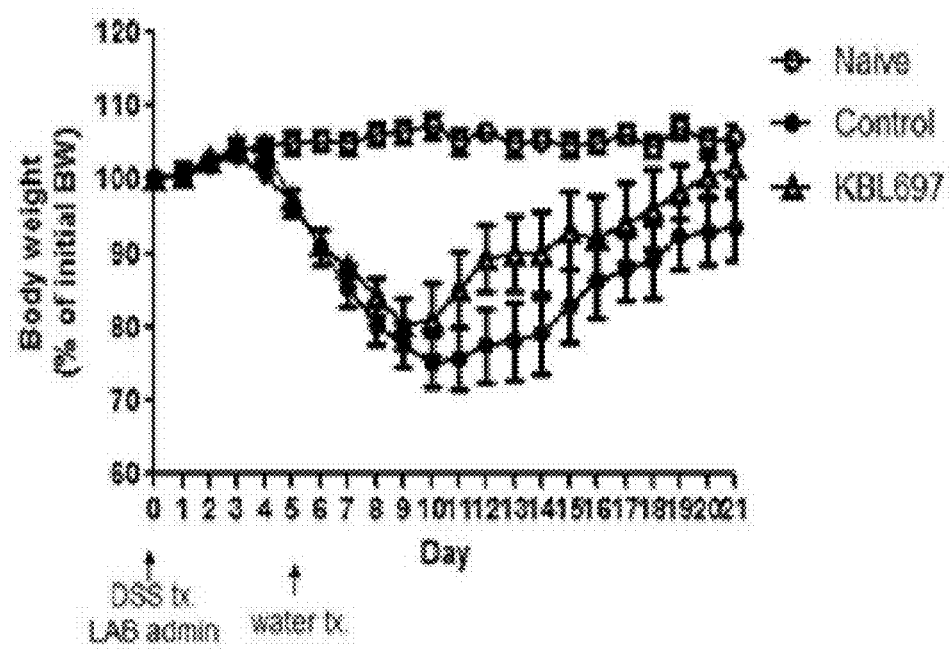
FIG. 14 illustrates the result of observation of the body weight recovering effect by the oral administration of *Lactobacillus gasseri* KBL697 strain at 1×10$^9$ CFU to mouse models that colitis was induced.
Figure 15:
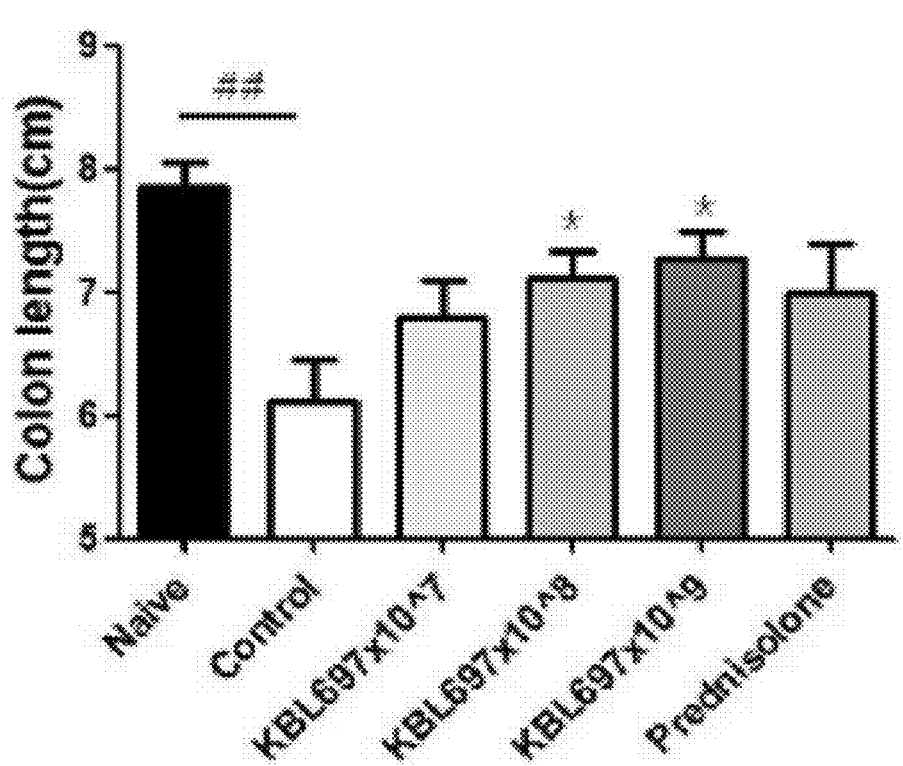
FIG. 15 illustrates the result of observation of the large intestine length recovering effect by the oral administration of *Lactobacillus gasseri* KBL697 strain to mouse models that colitis was induced.
Figure 17B:
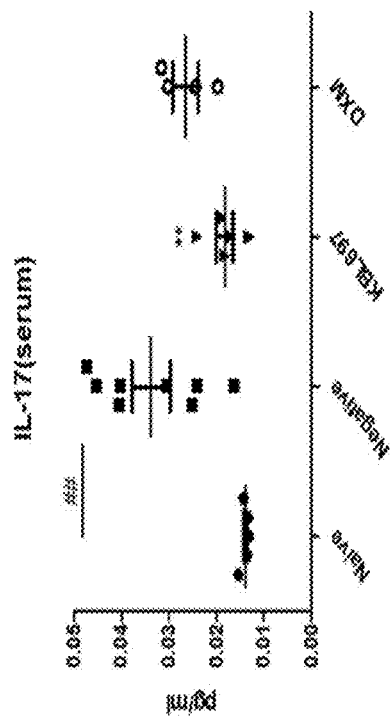
FIGS. 17A-17D illustrate the determination results of the effect of lowering inflammatory cytokines (TNF-α, IFN-γ, IL-17) by *Lactobacillus gasseri* KBL697 strain in mouse models that psoriasis was induced.
Figure 17A:
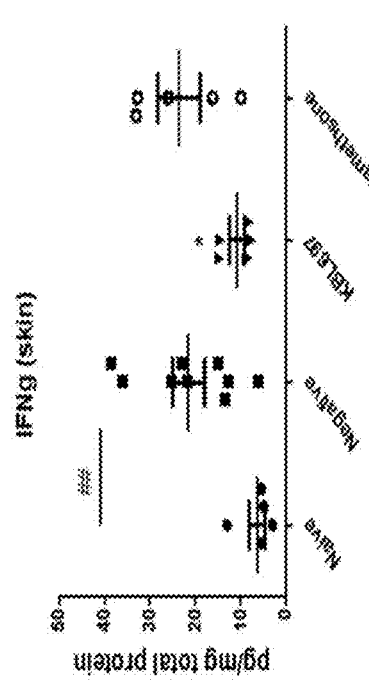
Figure 17D:
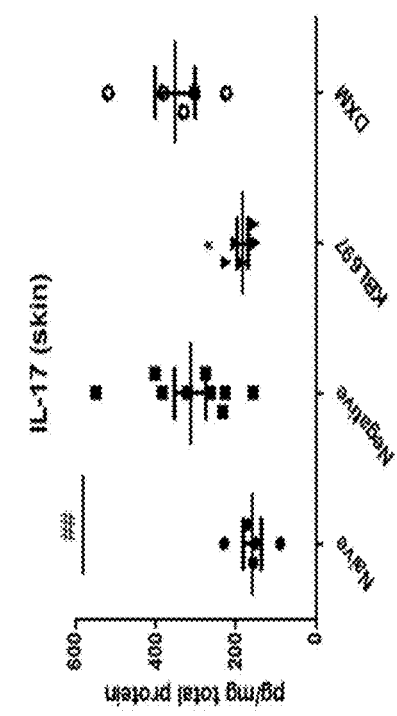
Figure 17C:
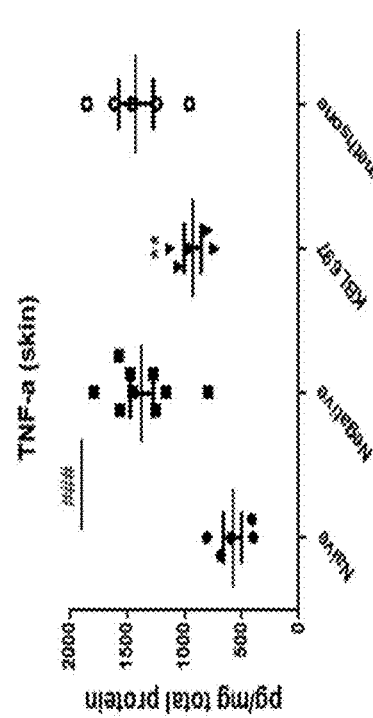

As a result, as shown in FIG. 14, it was found that in the colitis-induced mice dosed with $1\times10^9$ CFU of KBL697, similarly to the mice in the control group, the body weight was decreased rapidly until $10^{th}$ day, and then gradually recovered to restore normal levels on the $21^{st}$ day. In particular, as shown in FIG. 15, in the mice orally administered with $1\times10^9$ CFU of KBL697 (KBL697×10^9), it was found that the length of the colon was recovered to 90% level of the Naive group, and the symptom of reducing the length of the colon was significantly alleviated, compared to the negative control group of less than 80%. As a result, it was found that KBL697 showed an effect of improving colitis disease.

Example 8. Effects of KBL697 on Treatment and Prevention of Psoriasis

In order to verify the effects of KBL697 on alleviation of psoriasis, Balb/c mouse models were used.

After dividing Balb/c mice into groups of five mice, the mice in the control group were orally administered with 200 µL of PBS daily for ten days, while the mice in the test group were orally administered with 200 µL of each test strain diluted in PBS at least $1\times10^9$ CFU/0.2 mL daily. Strains and the control group were prepared in a same manner as Example 7. Two weeks after administering the bacteria, the back of each mouse was epilated from the lower end of the ear to the middle of the back, and mice were left for 24 hours. Then, 62.5 mg of 5% imiquimod cream was applied to the epilated portion once a day, causing psoriasis. After inducing psoriasis, the mice in the positive control group were administered with 200 µL of dexamethasone (0.25 mg/mL) daily. The same amount of KBL697 was administered daily even during psoriasis was induced. For ten days that psoriasis was induced, psoriasis area and severity index (PAST) of mice in the control and test groups was measured at two day intervals, and on the 10th day after psoriasis was induced, the skin thickness of each mouse was measured, and then the mouse was subjected to autopsy to determine the concentration of cytokines in skin tissues and in blood.

8-1. PASI Measurement and Changes in Skin Thickness

In order to evaluate imiquimod-induced skin psoriasis lesions, the PASI score was measured by the following method. Three indicators of erythema, scaling, and thickness of the skin were checked. And a condition with no lesions was scored as point 0, a mild condition as point 1, a moderate condition as point 2, a severe condition as point 3, and a very severe condition as point 4, and the total score was evaluated.

As a result, as shown in FIGS. 16A-E, PASI was significantly reduced in the imiquimod-induced psoriasis group dosed with KBL697 similarly to the positive control group dosed with dexamethasone (DXM), compared to the control group (NC) where psoriasis was induced. In addition, as a result of measuring the ear and dorsal skin thicknesses of mice using calipers and observing the effect on relief of edema symptom due to psoriasis, as shown in FIGS. 16F and 16G, it was found that the ear and dorsal skin thicknesses were significantly reduced in the test group dosed with KBL697, similarly to the positive control group.

8-2. Cytokine Measurement

In the case of psoriasis, reactions of Th1 cytokines such as IFN-γ and TNF-α, as well as Th17 responses, representatively IL-17, have been known to play an important role in the development and exacerbation of symptoms (Brembilla N C, *Front Immunol.* 2018). Mice with psoriasis induced by imiquimod were subjected to autopsies to determine the concentration of cytokines in skin tissues and in blood. The concentration of cytokines was determined with the protein sample taken in skin tissues and the serum sample prepared from blood in a same manner as Example 5-4 by using each of Mouse TNF-α ELISA Set (Cat No. 555138, BD OptEIA™) Mouse IFN-γ ELISA Set (Cat No. 558534, BD OptEIA™), Mouse IgE ELISA Set (Cat No. 555248, BD OptEIA™), and Mouse IL-17 DuoSet ELISA (Cat No. DY421-05, R&D SYSTEMS) kit.

As can be seen in FIGS. 17A-D, it was confirmed that inflammatory cytokines such as TNF-α and IFN-γ in skin tissues increased in psoriasis-induced mice were reduced by KBL697. In addition, it was confirmed that IL-17 specific to Th17 was also increased in psoriasis-induced skin tissues and serum, but decreased by KBL697 administration. As a result, it was confirmed that the administration of KBL697 could reduce the inflammatory cytokines which increased specifically when psoriasis was onset, exhibiting effects on the treatment or prevention of the disease through the reduction effect.

Example 9. Effects on Treatment and Prevention of Colitis Upon Concurrent Administration of Antibody for Treating Colitis and KBL697

Infliximab (product name Remicade) is a therapeutic recombinant antibody drug used as an injection for autoimmune diseases such as rheumatoid arthritis, ankylosing spondylitis, ulcerative colitis, Crohn's disease in adults, Crohn's disease in children, psoriasis, and psoriatic arthritis. The purpose of this study was to confirm the effect of improving intestinal disease symptoms in vivo in the case of concurrent administration of KBL697 and infliximab.

After dividing C57BL/6 mice into groups of eight mice, the mice were fed tap water with 2% DSS dissolved therein for 8 days (D0 to D7), inducing colitis. At the same time, 200 µL of PBS was orally administered to the mice in the control group for 14 days (D0 to D13) daily, while 200 µL of the KBL697 strain diluted in PBS to $1\times10^{10}$ CFU/mL was orally administered to the mice in the group dosed with KBL697 so that the amount of daily administration could be set at $2\times10^9$ CFU. In the therapeutic antibody administration group, infliximab antibody was administered once every 3 days to be a dose of 5 mg/kg per mouse, and 200 µL of PBS was orally administered daily during the period that the KBL697 strain was administered. In the test group for concurrent administration, 200 µL of the solution of KBL697 strain diluted in PBS to be $1\times10^{10}$ CFU/ml was orally administered every day, and on the third day, infliximab antibody was injected intravenously to be a dose of 5 mg/kg per mouse. The test groups without infliximab antibody administration were injected intravenously with the same volume of PBS. During the 14 days in which colitis was induced by DSS, the body weight changes of the mice in the control group and each test group were measured daily, and on the 14$^{th}$ day after DSS was supplied (D14), mice were subjected to autopsies to measure the length of the colon.

Figure 18A:
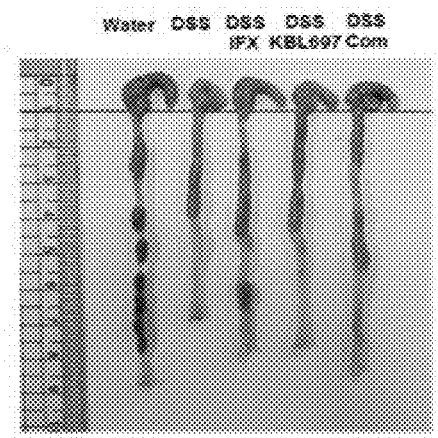
FIGS. 18A-18C illustrate the results of comparing the effect of recovering body weight and the length of the large intestine by *Lactobacillus gasseri* KBL697 strain and infliximab in mouse models that colitis was induced.
Figure 18B:
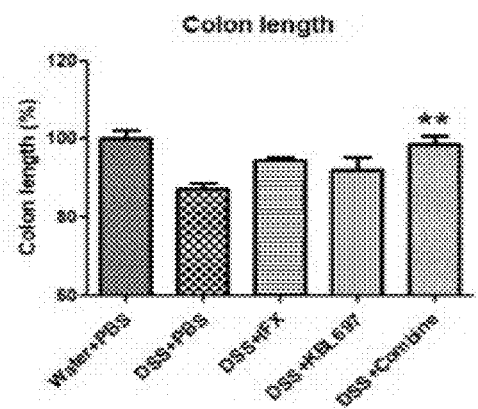

As a result, as shown in FIGS. 18A and 18B, regarding the colon length change, the width of decrease in the colon length was significantly improved in the groups that KBL697 was administered alone (DSS+KBL697) and that infliximab was administered alone (DSS+IFX), compared to the mice in the control group (DSS+PBS). In the group that infliximab and KBL697 were concurrently administered (DSS+Combine), it was confirmed that there was a significant improvement in colon length compared to the group that infliximab or KBL697 was administered alone.

Figure 18C:
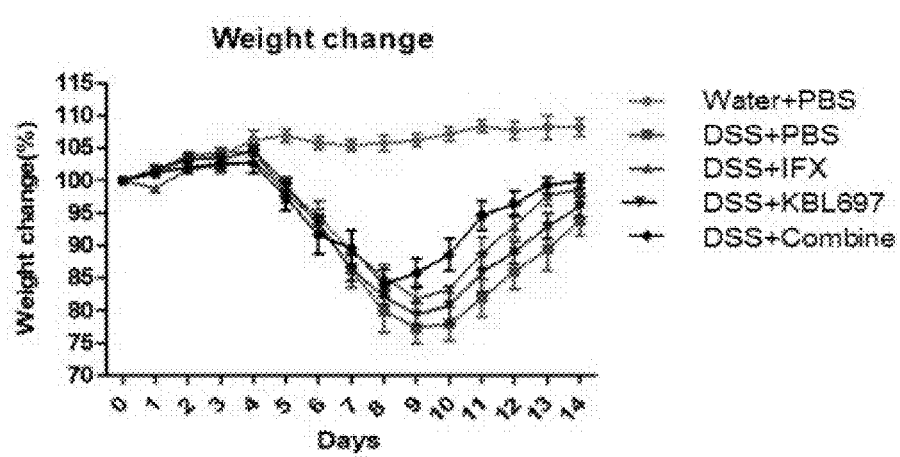

Regarding the change in body weights, as shown in FIGS. 18C and 18D, when 14 days elapsed after the administration, the effect on body weight decrease was significantly improved in the groups that KBL697 was administered alone (DSS+KBL697) and that infliximab was administered alone (DSS+IFX), compared to the mice in the control group with no treatment. When three days elapsed after the administration, it was confirmed that high body weights were maintained in the group that infliximab and KBL697 were concurrently administered (DSS+Combine), compared to all test groups that DSS was administered, verifying the effect of alleviating the symptom of body weight decrease due to inducement of colitis. Accordingly, regarding the use of said strain for the treatment of irritable bowel syndrome, it was confirmed that a stronger therapeutic effect could be expected when the strain was administered in combination with the commercially available therapeutic antibodies.

Specific aspects of the present invention have been described in detail above, and it is obvious to those skilled in the art that these specific aspects are only preferred embodiments, and the scope of the present invention is not limited thereby. Therefore, the scope of the present invention is substantially defined by the following claims, with equivalents to the claims Name of Depository Organization: Korean Collection for Type Cultures, Korea Research Institute of Bioscience and Biotechnology (KRIBB), 181, Ipsin-gil, Jeongeup-si, Jeollabuk-do, 56212, Republic of Korea.
Accession No.: KCTC13520BP
Accession Date: 20180427

INDUSTRIAL APPLICABILITY

The strain of Lactobacillus gasseri KBL697 (Accession No. KCTC 13520BP) according to the present invention attenuates allergic reactions of cells, significantly improves symptoms of atopic dermatitis, and exhibits anti-inflammatory, immunoregulatory and anti-fungal effects and a therapeutic effect on intestinal diseases such as irritable bowel syndrome and colitis. Thus, the single strain alone can achieve all the purposes of alleviating allergic diseases and inflammatory diseases, improving intestinal health, and immunoregulation, thereby finding advantageous applications as a probiotic substance. In addition, the strain, based on the anti-fungal activity thereof, can be advantageously utilized in a skin external preparation against various skin diseases caused by fungi, and in a cosmetic composition and a functional patch for alleviating sensitive skin.

SEQUENCE LIST FREE TEXT

An electronic file of Sequence List attached

The invention claimed is:

1. A method for alleviation of allergic symptom, alleviation of inflammatory symptom, improvement of intestinal health or immunoregulation, comprising administering a composition comprising at least one selected from *Lactobacillus gasseri* KBL697 strain with Accession No. KCTC 13520BP, cultures of said strain and lysates of said strain wherein said strain comprises 16S rDNA sequence of SEQ ID NO: 1, wherein the allergic symptoms can be alleviated by inhibiting the expression of IL-4 and IL-5 and secretion of histamine, the inflammatory symptoms can be alleviated by increasing the secretion of IL-10 and inhibiting the secretion of TNF-α and IL-6, the intestinal health can be improved by increasing the expression of proteins involved in the tight junction of enterocytes, and the immunoregulation can be achieved by inhibiting the secretion of TNF-α, IFN-γ and IL-17.

2. The method according to claim 1, wherein said allergic symptoms are selected from atopic dermatitis, eczema, allergic asthma, allergic rhinitis, allergic conjunctivitis or food allergy; said alleviation of intestinal health is the alleviation of at least one selected from abdominal bloating, abdominal discomfort, infectious diarrhea caused by pathogenic microorganisms, gastrocolitis, inflammatory bowel diseases, neurogenical intestinitis syndrome, irritable bowel syndrome, overgrowth of small intestinal microorganisms and intestinal feeding diarrhea.

3. The method according to claim 1, wherein the composition is feed composition.

4. A method for treating fungal infection comprising administering an anti-fungal composition comprising at least one selected from *Lactobacillus gasseri* KBL697 strain with Accession No. KCTC 13520BP, cultures of said strain, lysates of said strain, wherein said strain comprises 16S rDNA sequence of SEQ ID NO: 1, wherein said composition exhibits anti-fungal activities to *Malassezia furfur*.

5. The method according to claim 4, wherein the anti-fungal composition is a skin external preparation.

6. A method for improving cutaneous allergy, skin urticaria, atopic dermatitis, psoriasis, mycotic infection or eczema, comprising administering at least one selected from *Lactobacillus gasseri* KBL697 strain with Accession No. KCTC 13520BP, cultures of said strain and lysates of said strain, wherein said strain comprises 16S rDNA sequence of SEQ ID NO: 1, wherein the cutaneous allergy, skin urticaria, atopic dermatitis, psoriasis, mycotic infection or eczema can be improved by at least one from inhibiting the expression of IL-4 and IL-5 and secretion of histamine, TNF-α, IL-6, IFN-γ and IL-17, increasing the secretion of IL-10 and expression of proteins involved in the tight junction of enterocytes.

7. A method for the treatment of allergic disease, inflammatory disease, intestinal disease or autoimmune disease, comprising administering at least one selected from *Lactobacillus gasseri* KBL697 strain with Accession No. KCTC 13520BP, cultures of said strain, and lysates of said strain, wherein said strain comprises 16S rDNA sequence of SEQ ID NO: 1, wherein the allergic disease can be treated by inhibiting the expression of IL-4 and IL-5 and secretion of histamine, the inflammatory disease can be treated by increasing the secretion of IL-10 and inhibiting the secretion of TNF-α and IL-6, the intestinal disease can be treated by increasing the expression of proteins involved in the tight junction of enterocytes, and the autoimmune disease can be treated by inhibiting the secretion of TNF-α, IFN-γ and IL-17.

8. The method according to claim 7, wherein said allergic disease is selected from eczema, allergic asthma, allergic rhinitis, atopic dermatitis, allergic conjunctivitis or food allergy.

9. The method according to claim 7, wherein said inflammatory disease is selected from edema, conjunctivitis, periodontitis, rhinitis, otitis media, chronic sinusitis, pharyngolaryngitis, tonsillitis, bronchitis, pneumonia, gastric ulcer, gastritis, colitis, gout, eczema, acne, atopic dermatitis, contact dermatitis, seborrheic dermatitis, ankylosing spondylitis, rheumatic fever, fibromyalgia, osteoarthritis, psoriatic arthritis, rheumatoid arthritis, peri-arthritis of the shoulder, tendinitis, tenosynovitis myositis, hepatitis, cystitis, nephritis, Sjogren's syndrome, myasthenia gravis, sepsis, vasculitis, bursitis, temporal arteritis or multiple sclerosis.

10. The method according to claim 7, wherein said intestinal disease is selected from abdominal bloating, abdominal discomfort, infectious diarrhea caused by pathogenic microorganisms, gastrocolitis, inflammatory bowel diseases, neurogenical intestinitis syndrome, irritable bowel syndrome, overgrowth of small intestinal microorganisms or intestinal feeding diarrhea.

11. The method according to claim 7, wherein said autoimmune disease is selected from psoriasis, psoriatic arthritis, rheumatoid arthritis, lupus, systemic scleroderma, atopic dermatitis, asthma, Guilian-Barre syndrome, myasthenia gravis, dermatomyositis, polymyositis, multiple sclerosis, autoimmune encephalomyelitis, polyarteritis nodosa, Hashimoto's thyroiditis, temporal arteritis, juvenile diabetes, alopecia areata, pemphigus, aphthous stomatitis, autoimmune hemolytic anemia, Wegener's granulomatosis, Sjogren's syndrome, Addison's disease, Crohn's disease, or Behcet's disease.

12. The method according to claim 7, wherein said composition is used in combination with at least one drug selected from infliximab, adalimumab, golimumab, abciximab, alemtuzumab, atlizumab, basiliximab, belimumab, bevacizumab, ipilimumab, brentuximab vecotin, canakinumab, capromab pendetide, catumaxomab, certolizumab pegol, cetuximab, daclizumab, denosumab, eculizumab, edrecolomab, efalizumab, efungumab, ertumaxomab, etanercept, etaracizumab, fontolizumab, gemtuzumab ozogamicin, girentuximab, ibritumomab tiuxetan, igovomab, imciromab, ipilimumab, labetuzumab, mepolizumab, motavizumab, natalizumab, nimotuzumab, nofetumomab merpentan, ofatumumab, omalizumab, oregovomab, palivizumab, panitumumab, pemtumomab, pertuzumab, ranibizumab, raxibacumab, rituximab, rovelizumab, ruplizumab, tacatuzumab tetraxetan, tefibazumab, tocilizumab, tositumomab, trastuzumab, ustekinumab, secukinumab, vedolizumab, visilizumab, votumumab, zalutumumab and zanolimumab.

13. A method according to claim 7, the method comprising administering pharmaceutical composition comprising at least one of said strain, the cultures of said strain and the lysates of said strain.

14. The method according to claim 6, the method comprising administering cosmetic composition comprising at least one of said strain, the cultures of said strain and the lysates of said strain.

15. The method according to claim 14, wherein the cosmetic composition is a cosmetic patch.

16. The method according to claim 1, wherein the composition is food composition.

17. The method according to claim 6, the method comprising administering a medical patch comprising at least one of said strain, the cultures of said strain and the lysates of said strain.

* * * * *